US009255938B2

(12) United States Patent
Mizumoto et al.

(10) Patent No.: US 9,255,938 B2
(45) Date of Patent: Feb. 9, 2016

(54) SAMPLE ANALYZER AND METHOD OF ANALYZING A SAMPLE

(71) Applicants: Sysmex Corporation, Kobe-shi, Hyogo (JP); Arkray, Inc., Kyoto-shi, Kyoto (JP)

(72) Inventors: Toru Mizumoto, Hyogo (JP); Keisuke Tsutsumida, Hyogo (JP); Takayoshi Izumi, Hyogo (JP); Koji Fujimoto, Kyoto (JP); Shinya Nakajima, Kyoto (JP)

(73) Assignee: SYSMEX CORPORATION, Hyogo (JP)

( * ) Notice: Subject to any disclaimer, the term of this patent is extended or adjusted under 35 U.S.C. 154(b) by 347 days.

(21) Appl. No.: 13/732,967

(22) Filed: Jan. 2, 2013

(65) Prior Publication Data

US 2013/0111978 A1 May 9, 2013

Related U.S. Application Data

(63) Continuation of application No. PCT/JP2011/065144, filed on Jul. 1, 2011.

(30) Foreign Application Priority Data

Jul. 2, 2010 (JP) ................ 2010-152530

(51) Int. Cl.
*G01N 35/02* (2006.01)
*G01N 35/10* (2006.01)
*G01N 35/00* (2006.01)

(52) U.S. Cl.
CPC ........ *G01N 35/1009* (2013.01); *G01N 35/0092* (2013.01); *G01N 35/1016* (2013.01); *G01N 2035/0094* (2013.01); *G01N 2035/1025* (2013.01)

(58) Field of Classification Search
CPC ................. G01N 2035/047; G01N 2035/1025
See application file for complete search history.

(56) References Cited

U.S. PATENT DOCUMENTS

| 2005/0036912 A1 | 2/2005 | Yamakawa et al. |
| 2007/0072301 A1 | 3/2007 | Fukuda et al. |
| 2010/0111767 A1 | 5/2010 | Yonekura et al. |

FOREIGN PATENT DOCUMENTS

| JP | 02-195259 A | 8/1990 |
| JP | 5-119043 A | 5/1993 |

(Continued)

OTHER PUBLICATIONS

International Preliminary Report on Patentability for International Application No. PCT/JP2011/065144, dated Feb. 12, 2013, 7 pages.

(Continued)

*Primary Examiner* — P. Kathryn Wright
(74) *Attorney, Agent, or Firm* — Brinks Gilson & Lione

(57) ABSTRACT

A sample analyzer includes a first measurement unit, a second measurement unit, a detection section which detects information about an amount of a sample in a sample container before the first measurement unit aspirates the sample in the sample container, and a control section. Based on a detection result by the detection section and based on information about a predetermined sample amount necessary for performing both in the first measurement unit and the second measurement unit, when the control section has determined that the amount of the sample in the sample container is insufficient for the predetermined sample amount, the control section controls the first measurement unit and the second measurement unit so as not to aspirate the sample in the sample container.

11 Claims, 13 Drawing Sheets

(56) References Cited

FOREIGN PATENT DOCUMENTS

| | | |
|---|---|---|
| JP | 06-102272 A | 4/1994 |
| JP | 07-120475 A | 5/1995 |
| JP | 08-278313 A | 10/1996 |
| JP | 09-127125 A | 5/1997 |
| JP | 09329597 A * | 12/1997 |
| JP | 11-094840 A | 4/1999 |
| JP | 2003-315348 A | 11/2003 |
| JP | 2005-037132 A | 2/2005 |
| JP | 2006-98219 A | 4/2006 |
| JP | 2010-107399 A | 5/2010 |

OTHER PUBLICATIONS

International Search Report for International Application No. PCT/JP2011/065144, dated Sep. 20, 2011, 2 pages.

Suzuki, Masataka, Marketing Division, Eiken Chemical Co., Ltd., Fully-automatic urine analysis device US-3100R of the urine analysis transportation system "US-AlphaN," and English language translation thereof, *Sysmex Journal Web*, vol. 7, No. 2, Jun. 23, 2006, 14 pages.

* cited by examiner

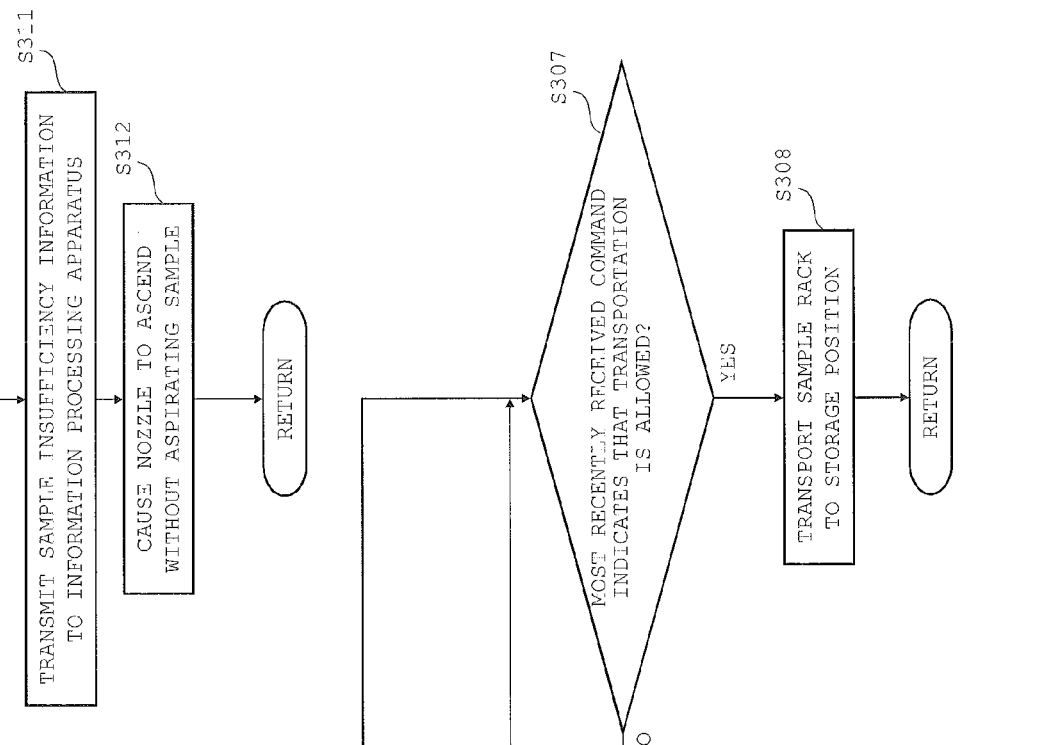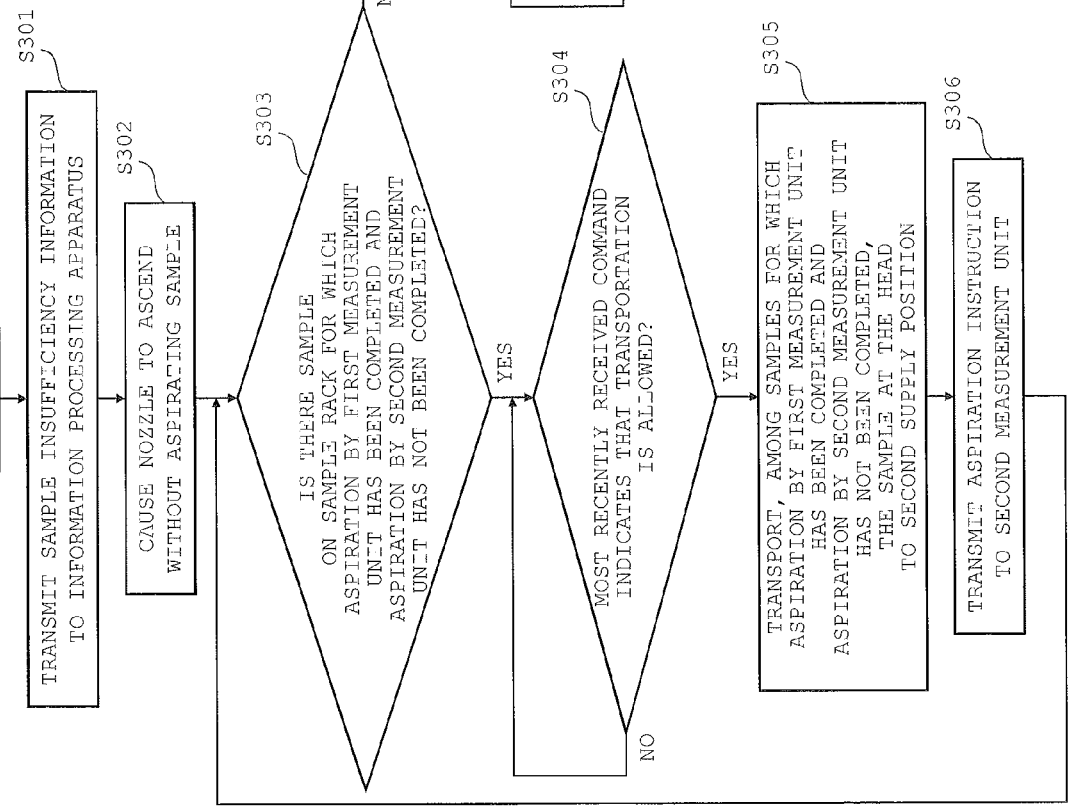

SAMPLE INSUFFICIENCY NOTIFICATION SCREEN

PROCESS OF DISPLAYING SAMPLE INSUFFICIENCY NOTIFICATION SCREEN PERFORMED BY INFORMATION PROCESSING APPARATUS

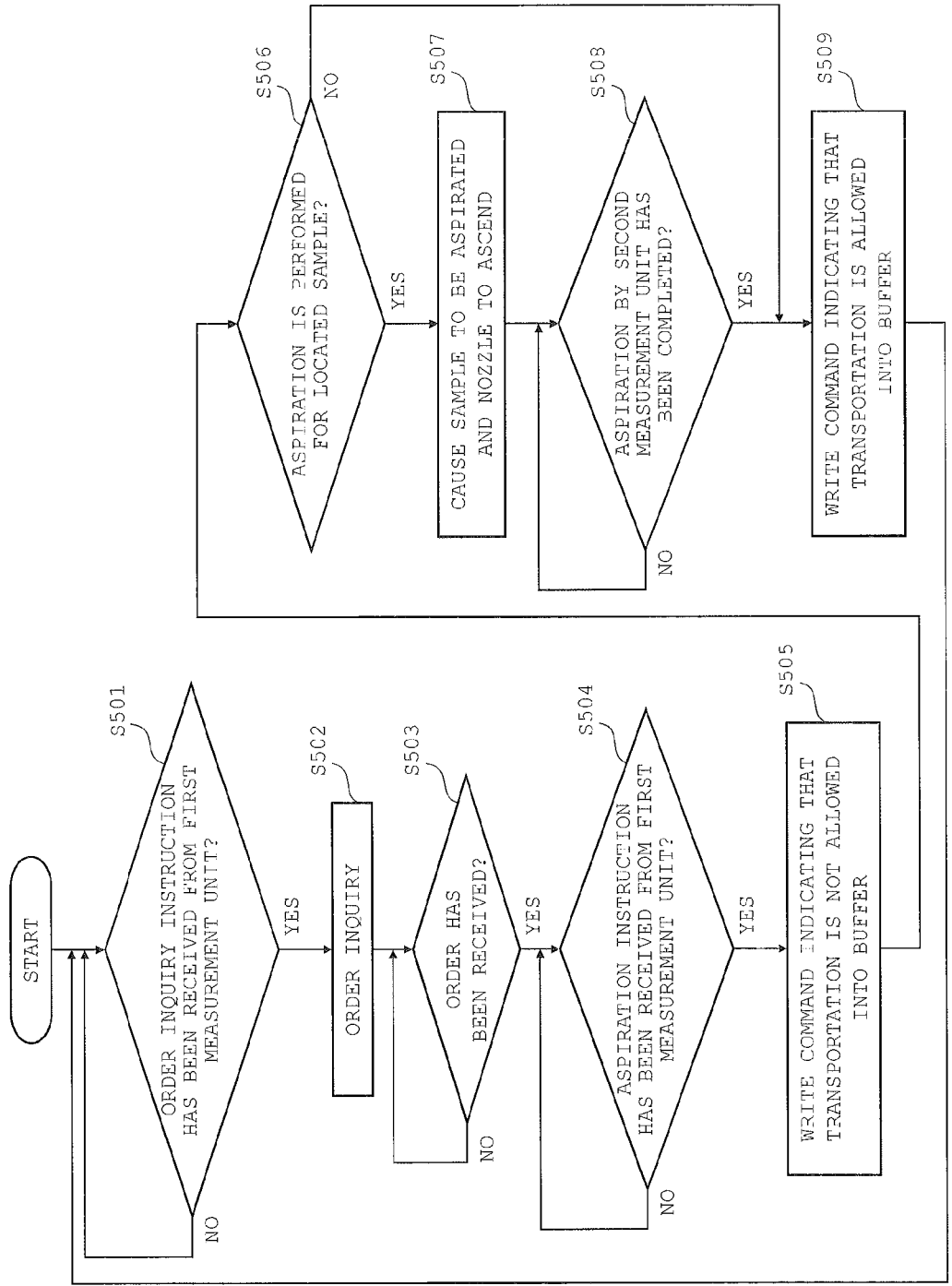

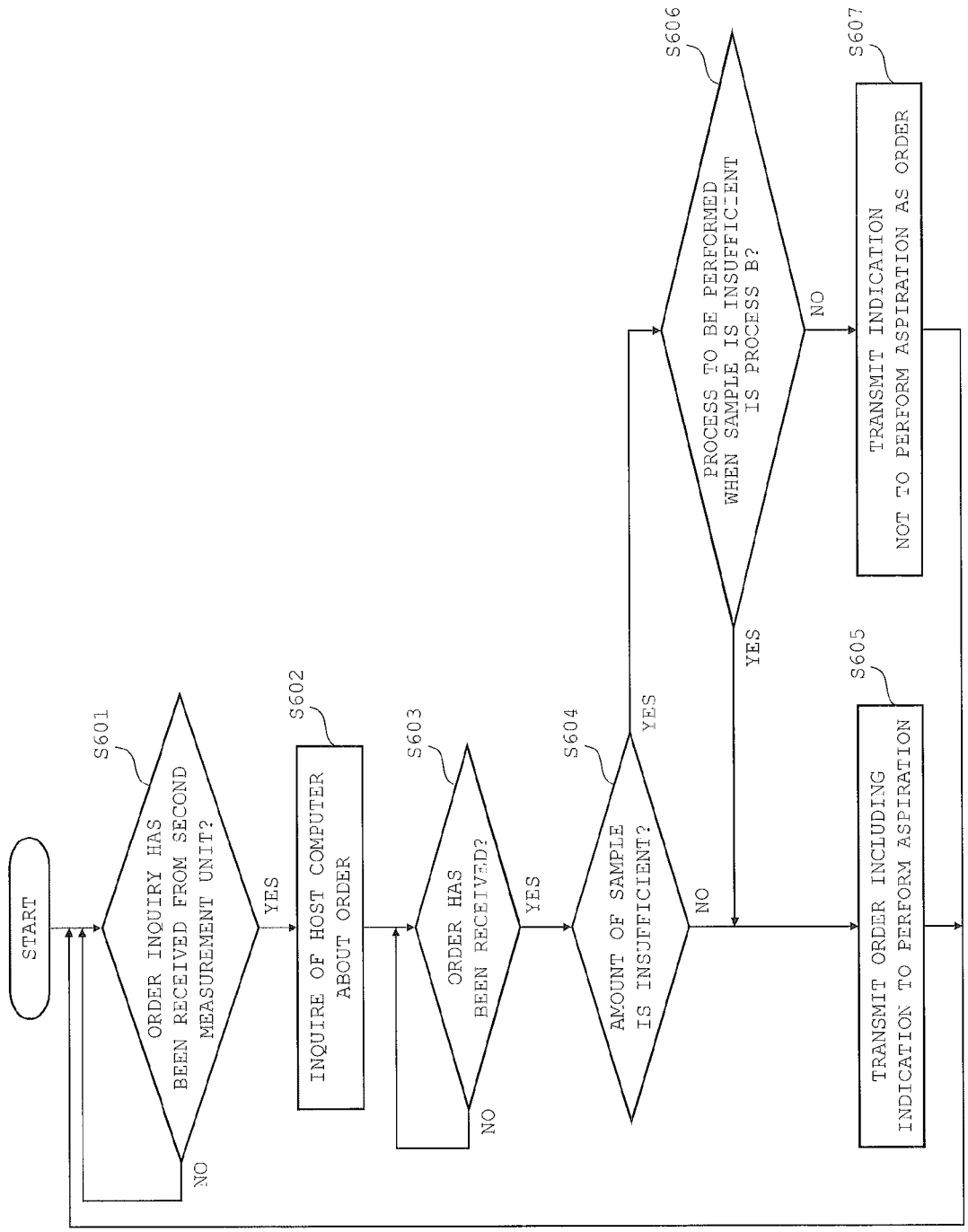
FIG.11 ORDER PROCESS PERFORMED BY INFORMATION PROCESSING APPARATUS

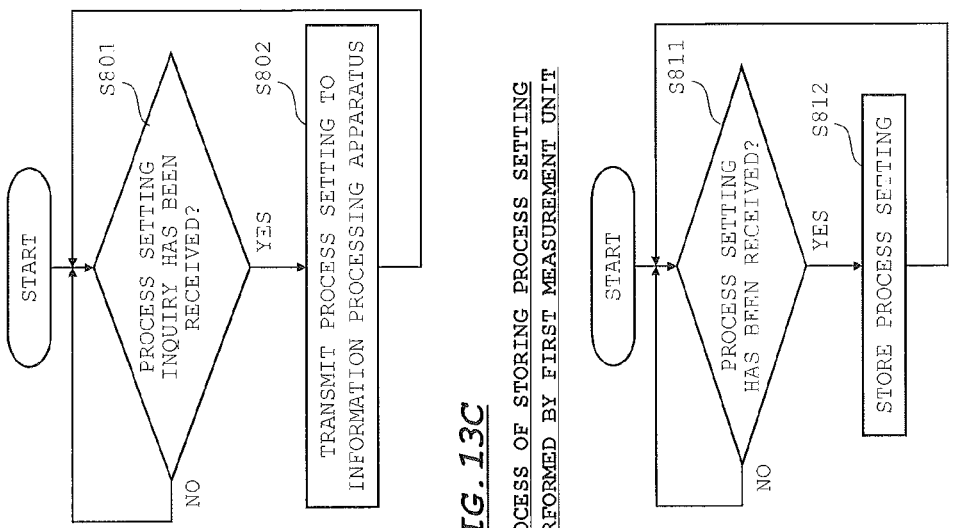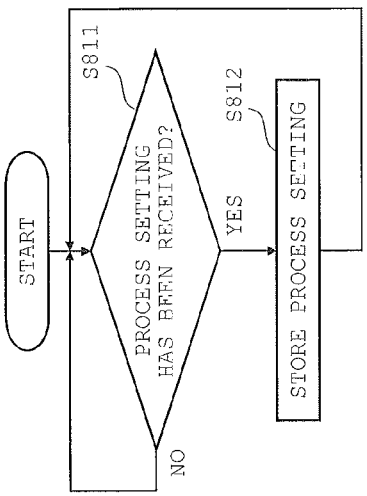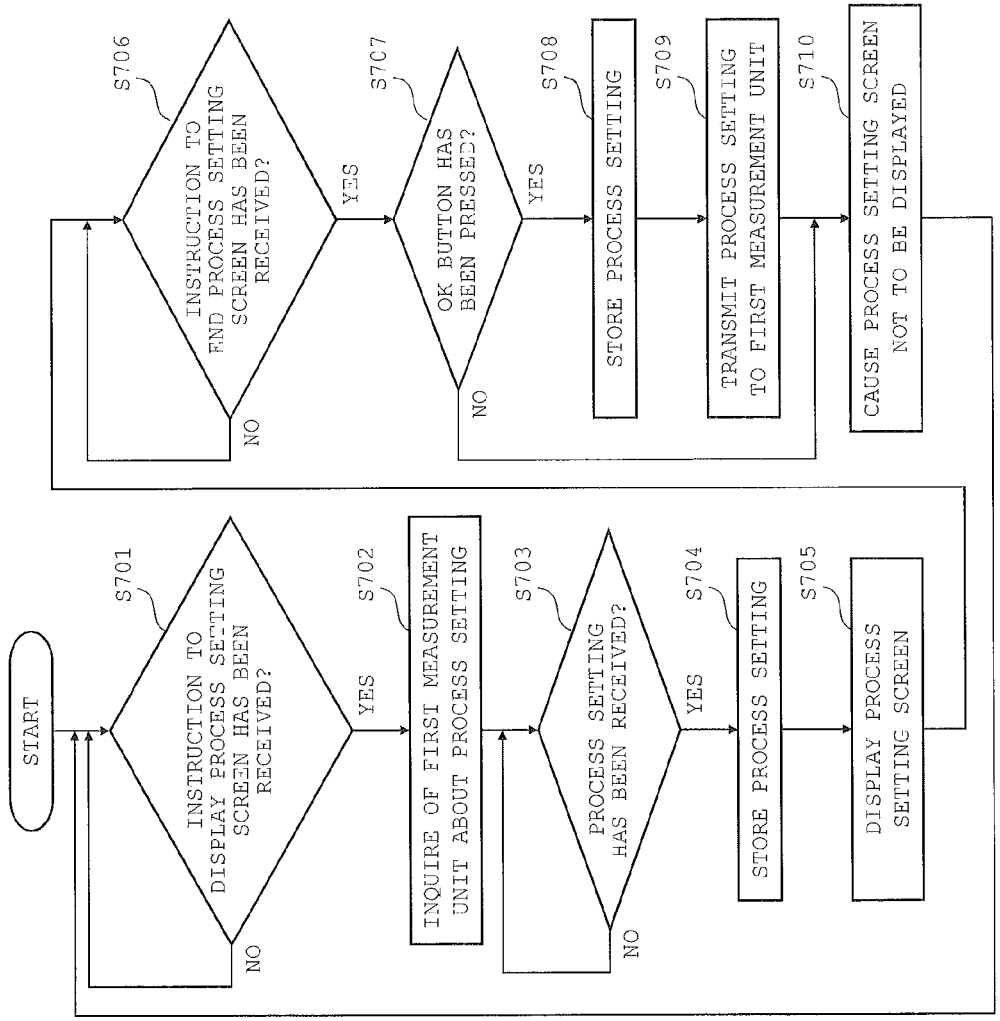

SAMPLE ANALYZER AND METHOD OF ANALYZING A SAMPLE

RELATED APPLICATIONS

This application is a continuation of PCT/JP2011/065144 filed on Jul. 1, 2011, which claims priority to Japanese Application No. 2010-152530 filed on Jul. 2, 2010. The entire contents of these applications are incorporated herein by reference.

BACKGROUND OF THE INVENTION

1. Field of the Invention

The present invention relates to sample analyzers in which a plurality of measurement units of different types are connected to each other by means of a transporting apparatus.

2. Disclosure of Related Art

There are known analyzers which detect the liquid amount of a sample by using a sensor before the sample is aspirated, and in which when the detected liquid amount is not sufficient for a liquid amount necessary for analysis of the sample, aspiration of the sample is stopped.

Further, in recent years, analyzers in which a plurality of measurement units of different types are connected to each other by means of a transporting apparatus are commercially available. Each measurement unit of such an analyzer is provided with an aspiration tube, and in the analyzer, a sample container is sequentially transported from an upstream measurement unit to a downstream measurement unit, and the sample is aspirated by each aspiration tube.

However, in a case where an analyzer having a liquid amount confirming function is applied to each of the plurality of measurement units connected to each other as mentioned above, when the liquid amount of the sample is sufficient for measurement performed by the most-upstream measurement unit but is not sufficient for measurement performed by a downstream measurement unit, the sample is aspirated by the most-upstream measurement unit and the sample having a remaining very small amount is transported to a downstream measurement unit. In such a case, there is a possibility that measurement by the downstream measurement unit cannot be performed, resulting in requirement of obtaining the sample again.

SUMMARY OF THE INVENTION

A first aspect of the present invention relates to a sample analyzer. The sample analyzer according to this aspect includes: a first measurement unit which aspirates a sample in a sample container to perform a first measurement; a second measurement unit which aspirates the sample in the sample container to perform a second measurement which is different from the measurement performed by the first measurement unit; a transporting apparatus which transports the sample container from the first measurement unit to the second measurement unit in this order; a detection section which detects information about an amount of the sample in the sample container before the first measurement unit aspirates the sample in the sample container; and a control section which determines, based on a detection result by the detection section and based on information about a predetermined sample amount that is necessary for performing measurements both in the first measurement unit and the second measurement unit, whether the amount of the sample in the sample container is sufficient for the predetermined sample amount, and which controls, when determining that the amount of the sample in the sample container is insufficient, the first measurement unit, the second measurement unit, and the transporting apparatus such that neither the first measurement unit nor the second measurement unit aspirates the sample in the sample container.

Here, "information about an amount of the sample" widely includes information that changes in accordance with the amount of the sample such as: the descent amount of a nozzle for aspirating the sample to reach the liquid surface of the sample from a reference position (for example, when the nozzle is driven by a stepping motor, the number of driving pulses supplied by the stepping motor); the time needed for the nozzle to reach the liquid surface of the sample from the reference position; the magnitude of the capacitance at the tip of the nozzle when detecting the liquid surface; and the like. Other than the above, the amount of the sample can be detected by using light, supersonic waves, image analysis, the weight of the sample, and the like. The "information about the amount of the sample" includes values and information obtained by such other methods.

In the sample analyzer according to this aspect, when the sample in a sample container is insufficient for performing measurements both in the first measurement unit and the second measurement unit, the sample is aspirated from the sample container by neither of the measurement units. Accordingly, before the sample is aspirated by the first measurement unit and the second measurement unit, the user can select an appropriate method (for example, measurement to be performed by one or both of the measurement units is switched to measurement to be performed manually, measurement using a diluted sample, or the like). Accordingly, it is possible to prevent occurrence of a situation where a sample is obtained from the patient again.

A second aspect of the present invention relates to a method of analyzing a sample executed by a sample analyzer comprising a first measurement unit for performing a first measurement and a second measurement unit for performing a second measurement which is different from the first measurement. The method according to this aspect includes steps of: (a) detecting information about an amount of a sample in a sample container; (b) determining, based on the detection result in the step (a) and based on information about a predetermined sample amount that is necessary for performing both of the first measurement and the second measurement, whether the amount of the sample in the sample container is sufficient for the predetermined sample amount; and (c) when the amount of the sample in the sample container is sufficient in the step (b), aspirating by the first measurement unit the sample in the sample container to perform the first measurement, and aspirating by the second measurement unit the sample in the sample container to perform the second measurement, and when the amount of the sample in the sample container is insufficient in the step (b), failing to aspirate by the first measurement unit and a second measurement unit.

BRIEF DESCRIPTION OF THE DRAWINGS

The above and other objects and new features of the present invention will be fully clarified by the following description of the embodiment, when read in conjunction with accompanying drawings.

FIG. 8A is a flow chart showing process A, and FIG. 8B shows processes B and C according to an embodiment;

FIG. 10 is a flow chart showing an aspiration process performed by the second measurement unit according to an embodiment;

FIG. 11 is a flow chart showing an order process performed by the information processing apparatus according to an embodiment;

FIG. 13A is a flow chart showing a process of displaying a process setting screen performed by the information processing apparatus, and FIGS. 13B and 13C are flow charts respectively showing a process of transmitting a process setting and a process of storing a process setting performed by the first measurement unit according to an embodiment.

It should be noted that the drawings are solely for description and do not limit the scope of the present invention by any degree.

DETAILED DESCRIPTION OF THE PREFERRED EMBODIMENTS

The present embodiment is realized by applying the present invention to a clinical sample analyzer which performs tests (urine qualitative tests) regarding urine protein, urine sugar, and the like, and tests (urinary sediment tests) regarding red blood cells, white blood cells, epithelial cells, and the like contained in urine. A urinary sediment test is performed on a sample for which it has been determined that a urinary sediment test is necessary as a result of a urine qualitative test performed on the sample. In the present embodiment, a plurality of sample containers respectively containing different samples are set in a rack, the rack is set in a sample analyzer, and testing of the samples are performed.

Hereinafter, a sample analyzer according to the present embodiment will be described with reference to the drawings.

In the present embodiment, a nozzle 11 and a sensor 13 correspond to a "detection section" described in claims. A CPU 101a and a CPU 201a correspond to a "control section" described in claims. A process setting screen 800 corresponds to a "setting selection section" described in claims. Process A corresponds to a "second setting" described in claims, process B corresponds to a "first setting" and a "third setting" described in claims, and process C corresponds to the "first setting" described in claims. A sample insufficiency notification screen 700 corresponds to a "notification section" described in claims. However, the correspondence between the claims and the present embodiment is merely an example, and does not limit the claims to the present embodiment.

Figure 1:
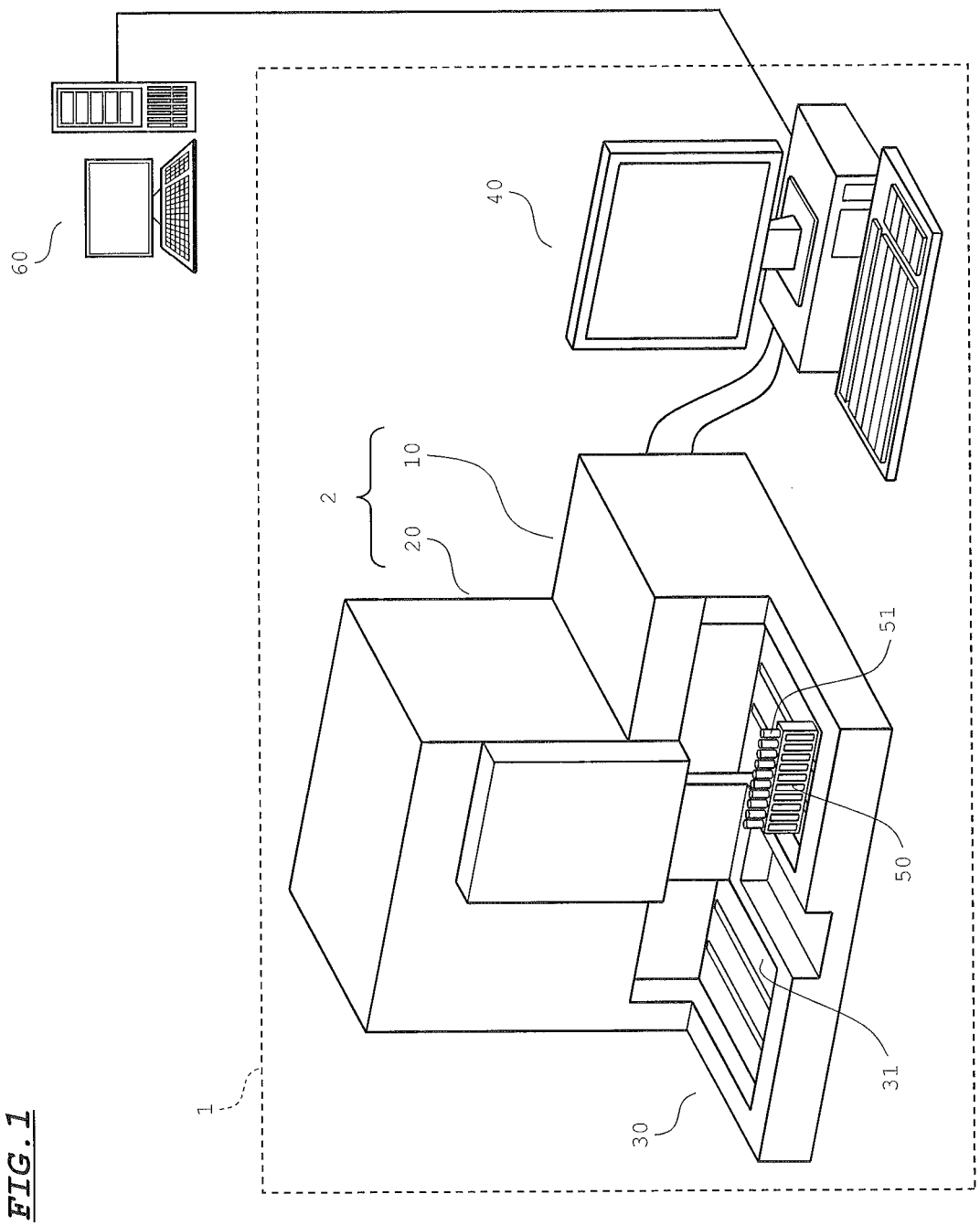
FIG. 1 shows an overall configuration of a system including a sample analyzer according to an embodiment.

FIG. 1 shows an overall configuration of a system including a sample analyzer 1. The sample analyzer 1 according to the present embodiment includes a sample measurement apparatus 2, a transporting apparatus 30, and an information processing apparatus 40.

The sample measurement apparatus 2 includes a first measurement unit 10 which performs urine qualitative tests and a second measurement unit 20 which performs urinary sediment tests. The first measurement unit 10 and the second measurement unit 20 are communicably connected to each other. Moreover, the first measurement unit 10 and the second measurement unit 20 are each communicably connected to the information processing apparatus 40. Further, the first measurement unit 10 is communicably connected to the transporting apparatus 30.

The transporting apparatus 30 is a single unit common for the first measurement unit 10 and the second measurement unit 20. The transporting apparatus 30 is mounted to the front face of the sample measurement apparatus 2 and includes a transport path 31. The transport path 31 has a bottom face of a flat plate shape, provided at a lower level than the upper face of the transporting apparatus 30. In a sample rack 50 which is transported on the transport path 31, ten holders are formed so as to be able to hold ten sample containers 51, respectively. By being held in a holder of the sample rack 50, each sample container 51 is transported on the transport path 31, along with the sample rack 50. A bar code label (not shown) for identifying a sample is affixed to a lateral side of the sample container 51. The information processing apparatus 40 is communicably connected to a host computer 60 via a communication line.

Figure 2:
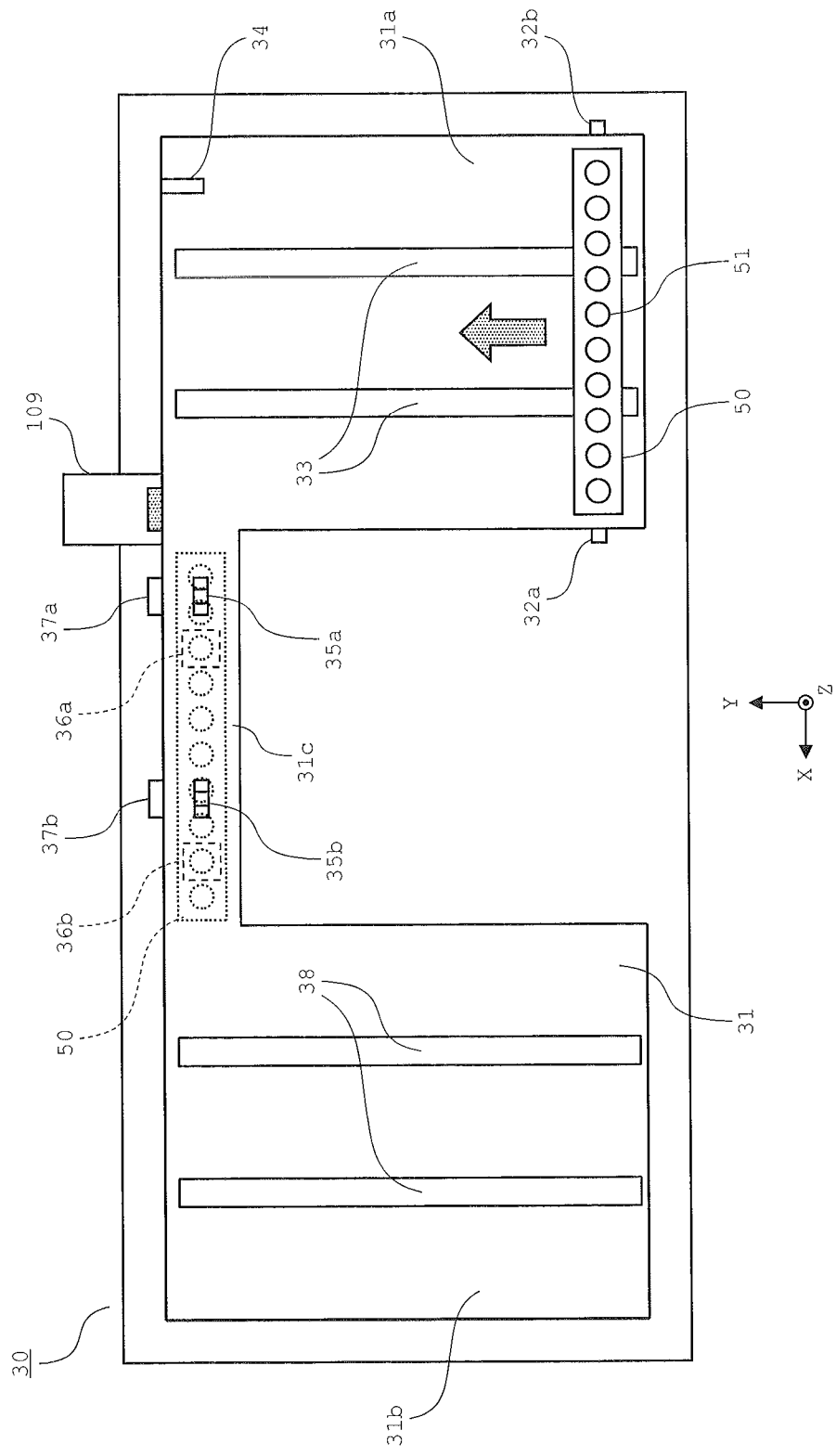
FIG. 2 is a plan view showing a configuration of a transporting apparatus according to an embodiment, viewed from above.

FIG. 2 is a plan view showing a configuration of the transporting apparatus 30, viewed from above.

The transporting apparatus 30 includes the transport path 31, transmissive sensors 32a and 32b, belts 33 and 38, a pushing-out mechanism 34, lateral transportation sensors 35a and 35b, and reflective sensors 37a and 37b. The transport path 31 includes a right vessel region 31a, a left vessel region 31b, and a connection region 31c. The right vessel region 31a and the left vessel region 31b are connected to each other by means of the connection region 31c.

The transmissive sensors 32a and 32b are composed of a light emitter and a light receiver, and detect a sample rack 50 located at the front side in the right vessel region 31a (at the end in the Y-axis negative direction). Based on an output signal from the sensors 32a and 32b, it is detected that a sample rack 50 is placed at the front side in the right vessel region 31a by a user. The belt 33 is provided in the right vessel region 31a, and moves the sample rack 50 placed in the right vessel region 31a in the Y-axis positive direction, to locate it to the rear side in the right vessel region 31a (at the end in the Y-axis positive direction).

The pushing-out mechanism 34 includes a driving section (not shown) further to the rear than the transport path 31, and is configured such that a pushing-out claw moves from the right rear of the right vessel region 31a to the left rear of the left vessel region 31b in the left-right direction (X-axis direction). In FIG. 2, only the claw of the pushing-out mechanism 34 is shown. By the pushing-out mechanism 34 pushing the right-end side face of the sample rack 50, the sample rack 50 located at the rear side of the right vessel region 31a is moved, via the connection region 31c, to the rear side of the left vessel region 31b. As will be described later, a process of transporting the sample rack 50 near the connection region 31c is performed as appropriate, in accordance with aspiration processes respectively performed by the first measurement unit 10 and the second measurement unit 20.

A bar code reader 109 reads out a sample number for identifying the sample container 51, from a bar code label affixed to the sample container 51 located, in the transport path 31, in front of (Y-axis negative direction) the bar code reader 109. It should be noted that the bar code reader 109 is provided in the first measurement unit 10 and is directly controlled by a CPU 101a of the first measurement unit 10 (see FIG. 4).

Each of the lateral transportation sensors 35a and 35b has a claw slightly projecting upward (Z-axis positive direction) from the bottom face of the transport path 31 (the connection region 31c). When the sample rack 50 is moved from right to left (X-axis positive direction), the states of the claws of the lateral transportation sensors 35a and 35b change between a projecting state and a non-projecting state relative to the bottom face of the transport path 31, in accordance with opening parts and non-opening parts which are formed in the bottom face of the sample rack 50 at intervals between holders for sample containers 51. Accordingly, it is determined as appropriate whether the distance by which the pushing-out mechanism 34 has been moved agrees with the distance by which the sample rack 50 has been moved.

A first supply position 36a and a second supply position 36b are positions at which samples contained in sample containers 51 are aspirated by the first measurement unit 10 and the second measurement unit 20, respectively.

When measurement is performed by the first measurement unit 10, a nozzle 11 (see FIGS. 3A and 3B) provided in the first measurement unit 10 is inserted into the sample container 51 located at the first supply position 36a. At this time, the liquid surface of the sample contained in the sample container 51 is detected. When it is determined that the sample is contained by a predetermined amount or more, the sample contained in the sample container 51 is aspirated by the nozzle 11. The aspirated sample is measured in the first measurement unit 10. When the aspiration is completed, the nozzle 11 is drawn from the sample container 51, and the sample rack 50 holding this sample container 51 is moved leftward by the pushing-out mechanism 34. The detection of the liquid surface of the sample performed when the nozzle 11 is inserted into the sample container 51 will be described later with reference to FIGS. 3A and 3B.

Further, when measurement is performed by the second measurement unit 20, a nozzle (not shown) provided in the second measurement unit 20 is inserted into the sample container 51 located at the second supply position 36b. Subsequently, the sample contained in the sample container 51 is aspirated by the nozzle. The aspirated sample is measured in the second measurement unit 20. When the aspiration is completed, the nozzle is drawn from the sample container 51, and the sample rack 50 holding this sample container 51 is moved leftward by the pushing-out mechanism 34.

The distance between the first supply position 36a and the second supply position 36b is set shorter than or equal to the distance between the sample container 51 held in the holder at the left end (at the end in the X-axis positive direction in FIG. 2) of the sample rack 50 and the sample container 51 held in the holder at the right end (at the end in the X-axis negative direction in FIG. 2). Moreover, the interval between the first supply position 36a and the second supply position 36b is set such that the sample containers 51 held in two different holders in one sample rack 50 are concurrently located at the first supply position 36a and the second supply position 36b, respectively. Accordingly, aspiration by the first measurement unit 10 and aspiration by the second measurement unit 20 can be concurrently performed.

The reflective sensors 37a and 37b detect whether holders of the sample rack 50 located, in the transport path 31, in front of (Y-axis negative direction) the reflective sensors 37a and 37b are holding sample containers 51, respectively. Accordingly, it is possible to confirm again whether the sample container 51 whose sample number was read by the bar code reader 109 is being held in a corresponding holder of the sample rack 50, before aspiration therefor is performed.

The belt 38 is provided in the left vessel region 31b, and moves the sample rack 50 located at the rear side (at the end in the Y-axis positive direction) of the left vessel region 31b, in the Y-axis negative direction, thereby locating it at the front side (at the end in the Y-axis negative direction) of the left vessel region 31b. Then, the sample rack 50 located at the front side of the left vessel region 31b is taken out by the user.

Figure 3A:
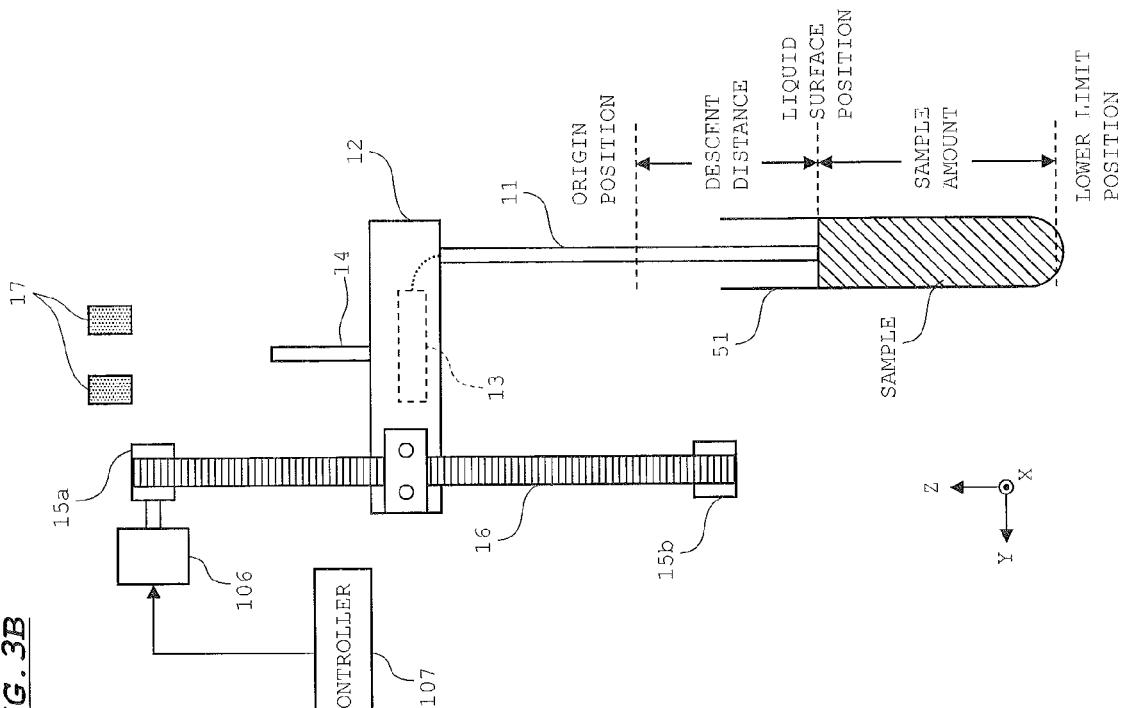
FIGS. 3A and 3B illustrate detection of the liquid surface of a sample performed when a nozzle is inserted into a sample container according to an embodiment.
Figure 3B:
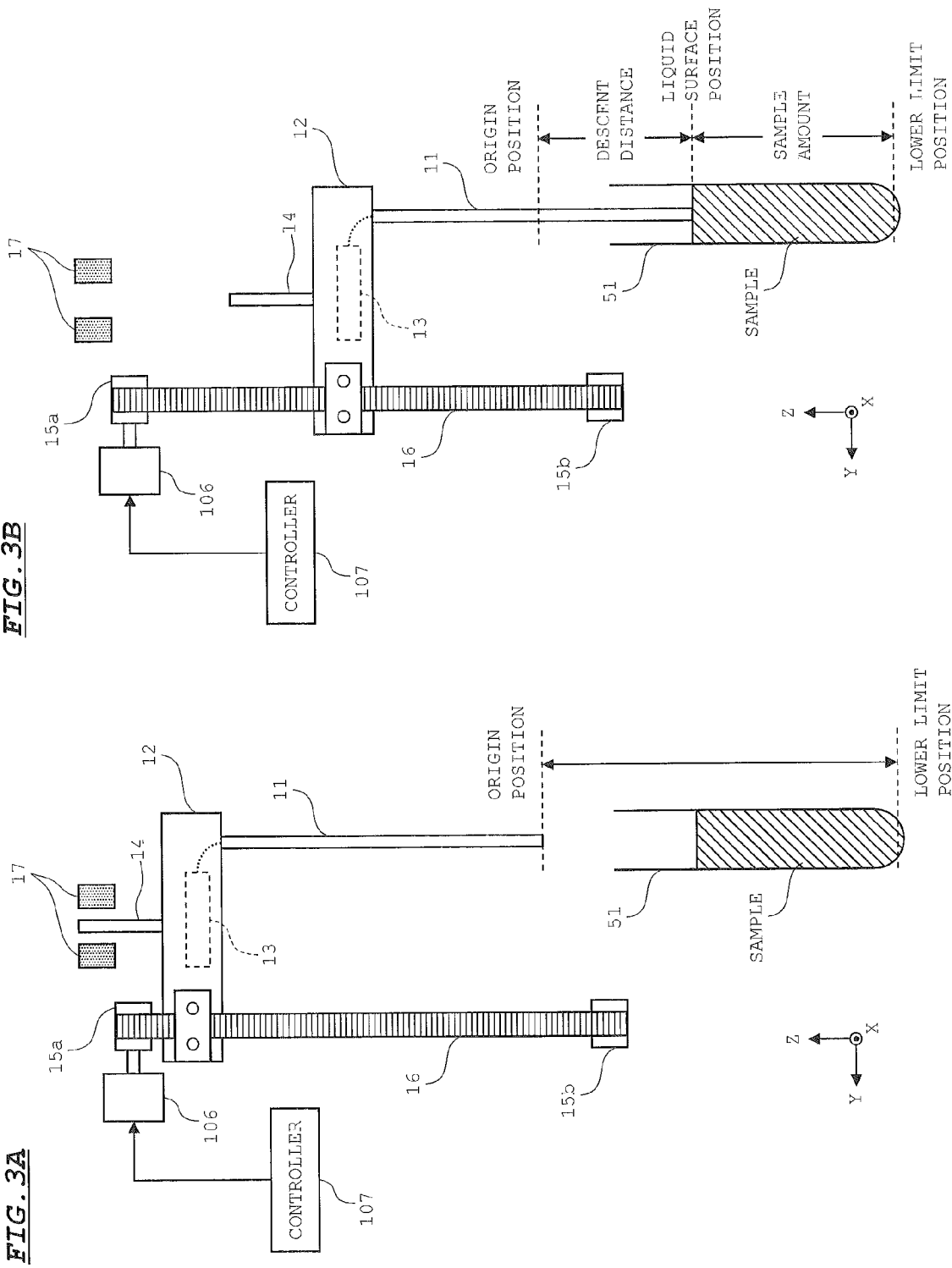

FIGS. 3A and 3B illustrate detection of the liquid surface of a sample performed when the nozzle 11 is inserted into a sample container 51. FIG. 3A is a schematic diagram of a state where the lower end of the nozzle 11 is set at the origin position, viewed sideways, and FIG. 3B is a schematic diagram of a state where the lower end of the nozzle 11 is contacting the liquid surface position, viewed sideways.

With reference to FIG. 3A or 3B, the nozzle 11 is formed of a conductive metal member, and is provided on a support 12. A pump (not shown) is connected to the nozzle 11, and the pump enables the nozzle 11 to aspirate a sample. The support 12 is provided with a capacitance-type sensor 13 and a light blocking plate 14. The sensor 13 is connected to the nozzle 11. The support 12 is supported by a guide mechanism (not shown) so as to be movable in the up-down direction (Z-axis direction).

Pulleys 15a and 15b, a belt 16, a stepping motor 106, a controller 107, and a sensor 17 are provided inside the first measurement unit 10. The pulleys 15a and 15b are provided so as to be rotatable about the Y-axis. The belt 16 is wound around the pulleys 15a and 15b. The support 12 is fixed to the belt 16, and the rotary shaft of the stepping motor 106 is connected to the pulley 15a.

The stepping motor 106 is driven based on pulse signals outputted from the controller 107. The controller 107 outputs pulse signals to the stepping motor 106, by the number of pulses specified by the CPU 101a (see FIG. 4) of the first measurement unit 10. When the stepping motor 106 is driven, the belt 16 is moved around the pulleys 15a and 15b, and the nozzle 11 and the support 12 are moved in the Z-axis direction. The sensor 17 is a transmissive sensor composed of a light emitter and a light receiver. As shown in FIG. 3A, when the lower end of the nozzle 11 is set at the origin position, the light blocking plate 14 is located between the light emitter and the light receiver of the sensor 17.

When detection of the liquid surface for the sample container 51 located under the nozzle 11 (at the first supply position 36a) is to be performed, the stepping motor 106 is first driven such that the light blocking plate 14 is located between the light emitter and the light receiver of the sensor 17. Accordingly, as shown in FIG. 3A, the lower end of the nozzle 11 is located at the origin position. From this state, the stepping motor 106 is driven such that the lower end of the nozzle 11 reaches a lower limit position. The lower limit position is set to be a position slightly above the bottom face of the sample container 51. It should be noted that in order to allow the lower end of the nozzle 11 to reach the lower limit position from the origin position, the number of pulses specified by the CPU 101a to the controller 107 (hereinafter referred to as "prescribed pulse number") is stored in advance in a storage section 101b (see FIG. 4) of the first measurement unit 10.

When the nozzle 11 is moved downward (Z-axis negative direction) and the lower end of the nozzle 11 is located at the liquid surface position as shown in FIG. 3B, it is detected, based on an output signal from the sensor 13, that the lower end of the nozzle 11 has contacted the liquid surface. The descent distance by which the nozzle 11 has been lowered is obtained based on the number of pulse signals outputted from the controller 107 to the stepping motor 106 during the time period from when the lower end of the nozzle 11 was at the origin position until it reached the liquid surface position (hereinafter referred to as "descent pulse number"). Further, the amount of the sample is obtained based on a value obtained by subtracting the descent pulse number from the prescribed pulse number (hereinafter referred to as "remaining pulse number"). Since sample containers having a predetermined shape and size are used in the sample measurement apparatus 2 of the present embodiment, the relationship between the liquid surface position and the amount of the sample is uniquely determined. Therefore, it is possible to obtain information about the amount of the sample by using the descent pulse number.

Figure 4:
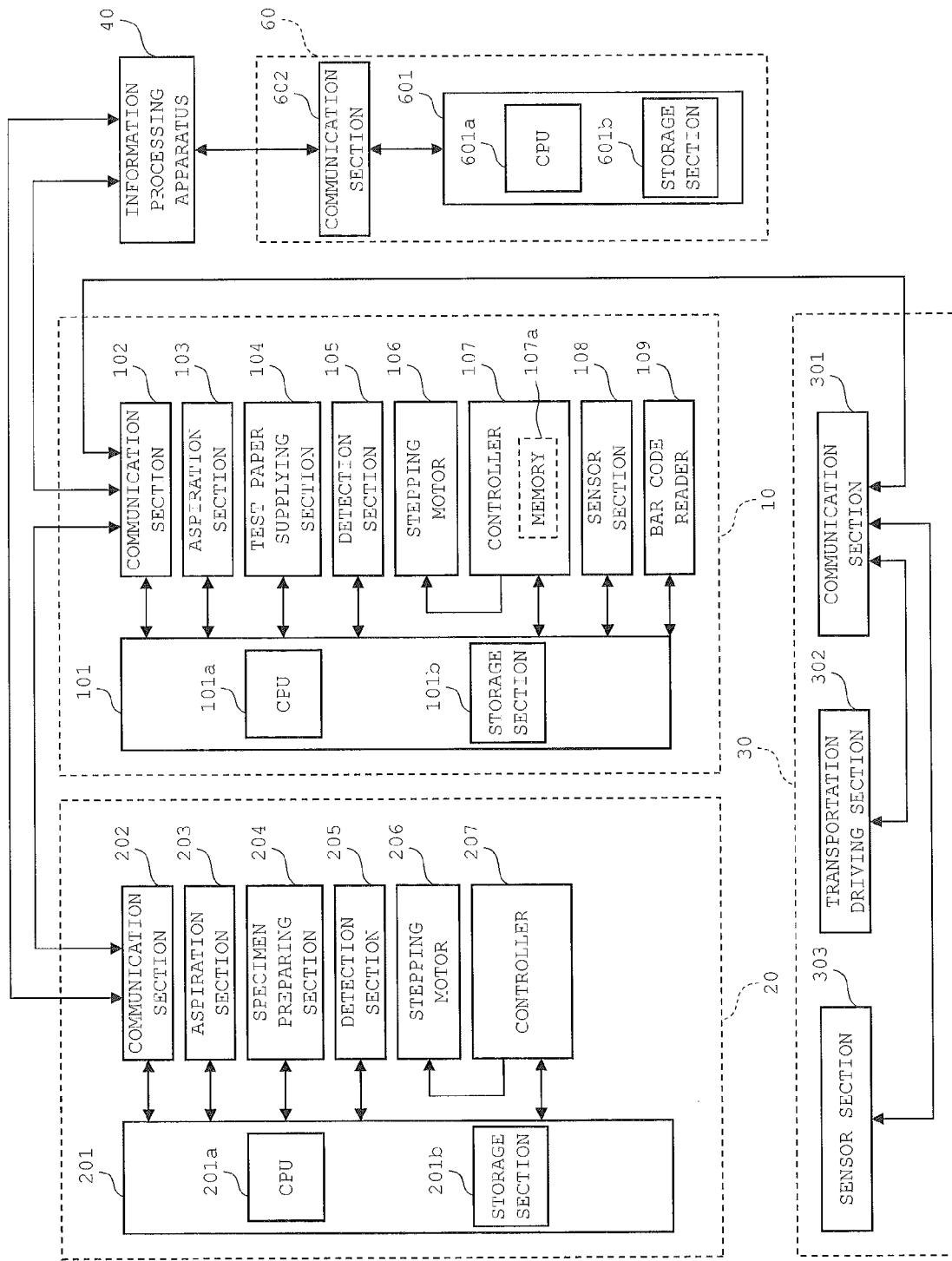
FIG. 4 shows configurations of a first measurement unit, a second measurement unit, a transporting apparatus, and a host computer according to an embodiment.

FIG. 4 shows configurations of the first measurement unit 10, the second measurement unit 20, the transporting apparatus 30, and the host computer 60.

The first measurement unit 10 includes a control section 101, a communication section 102, an aspiration section 103, a test paper supplying section 104, a detection section 105, the stepping motor 106, the controller 107, a sensor section 108, and the bar code reader 109.

The control section 101 includes the CPU 101a and the storage section 101b. The CPU 101a executes computer programs stored in the storage section 101b and controls sections of the first measurement unit 10. Moreover, the CPU 101a controls sections of the transporting apparatus 30 via the communication section 102. The storage section 101b includes storage means such as a ROM, a RAM, and a hard disk.

The communication section 102 processes signals from the control section 101 to output the resultant signals to the second measurement unit 20, the transporting apparatus 30, and the information processing apparatus 40, and processes signals from the second measurement unit 20, the transporting apparatus 30, and the information processing apparatus 40 to output the resultant signals to the control section 101. The aspiration section 103 aspirates the sample in the sample container 51 located at the first supply position 36a via the nozzle 11 of the first measurement unit 10. The test paper supplying section 104 takes out test paper necessary for measurement from a test paper feeder in which test paper is stored, and applies as a spot the sample aspirated by the aspiration section 103 onto the taken-out test paper. The detection section 105 measures the test paper on which the sample has been applied as a spot. A measurement result obtained by the measurement is outputted to the control section 101 and analyzed by the CPU 101a.

The stepping motor 106 is driven based on pulse signals outputted from the controller 107. The controller 107 outputs pulse signals to the stepping motor 106 by the number of pulses specified by the CPU 101a. Further, the controller 107 includes a memory 107a. The memory 107a has stored therein the number of pulse signals outputted from the controller 107 to the stepping motor 106, and information whether pulse signals were outputted to the stepping motor 106 by the number of pulses specified by the CPU 101a.

Every time the controller 107 outputs pulse signals to the stepping motor 106, the controller 107 updates the number of pulse signals stored in the memory 107a, and updates the information whether pulse signals were outputted by the specified number of pulses.

The sensor section 108 includes the sensors 13 and 17 shown in FIGS. 3A and 3B. Output signals from the sensor section 108 and the sample number read by the bar code reader 109 are outputted to the control section 101.

The second measurement unit 20 includes a control section 201, a communication section 202, an aspiration section 203, a specimen preparing section 204, a detection section 205, a stepping motor 206, and a controller 207.

The control section 201 includes a CPU 201a and a storage section 201b. The CPU 201a executes computer programs stored in the storage section 201b and controls sections of the second measurement unit 20. The storage section 201b includes storage means such as a ROM, a RAM, and a hard disk.

The communication section 202 processes signals from the control section 201 to output the resultant signals to the first measurement unit 10 and the information processing apparatus 40, and processes signals from the first measurement unit 10 and the information processing apparatus 40 to output the resultant signals to the control section 201. The aspiration section 203 aspirates the sample in the sample container 51 located at the second supply position 36b via a nozzle (not shown) of the second measurement unit 20. The specimen preparing section 204 mixes and stirs the sample aspirated by the aspiration section 203 and a reagent necessary for measurement, to prepare a specimen for measurement to be performed by the detection section 205. The detection section 205 measures the specimen prepared by the specimen preparing section 204. A measurement result obtained by the measurement is outputted to the control section 201.

The stepping motor 206 is driven based on pulse signals outputted from the controller 207, and moves the nozzle of the second measurement unit 20 in the up-down direction, similarly to the stepping motor 106 of the first measurement unit 10. The controller 207 outputs pulse signals to the stepping motor 206 by the number of pulses specified by the CPU 201a.

The transporting apparatus 30 includes a communication section 301, a transportation driving section 302, and a sensor section 303. The communication section 301 processes signals from the first measurement unit 10 to output the resultant signals to sections of the transporting apparatus 30, and processes signals from sections of the transporting apparatus 30 to output the resultant signals to the first measurement unit 10.

The transportation driving section 302 is controlled by the CPU 101a of the first measurement unit 10. It should be noted that the transportation driving section 302 includes mechanisms for driving the belts 33 and 38 and the pushing-out mechanism 34 shown in FIG. 2. The sensor section 303 outputs output signals from various sensors, to the first measurement unit 10 via the communication section 301. It should be noted that the sensor section 303 includes the sensors 32a and 32b, the lateral transportation sensors 35a and 35b, and the sensors 37a and 37b shown in FIG. 2.

The host computer 60 includes a control section 601 and a communication section 602. The control section 601 includes a CPU 601a and a storage section 601b. The CPU 601a executes computer programs stored in the storage section 601b. Also, when receiving an order inquiry from the information processing apparatus 40, the CPU 601a returns an order stored in the storage section 601b. Moreover, the CPU 601a determines an order for the second measurement unit 20, based on an analysis result received from the first measurement unit 10 via the information processing apparatus 40 and based on measurement requiring criteria stored in the storage section 601b. The storage section 601b includes storage means such as a ROM, a RAM, and a hard disk.

Figure 5:
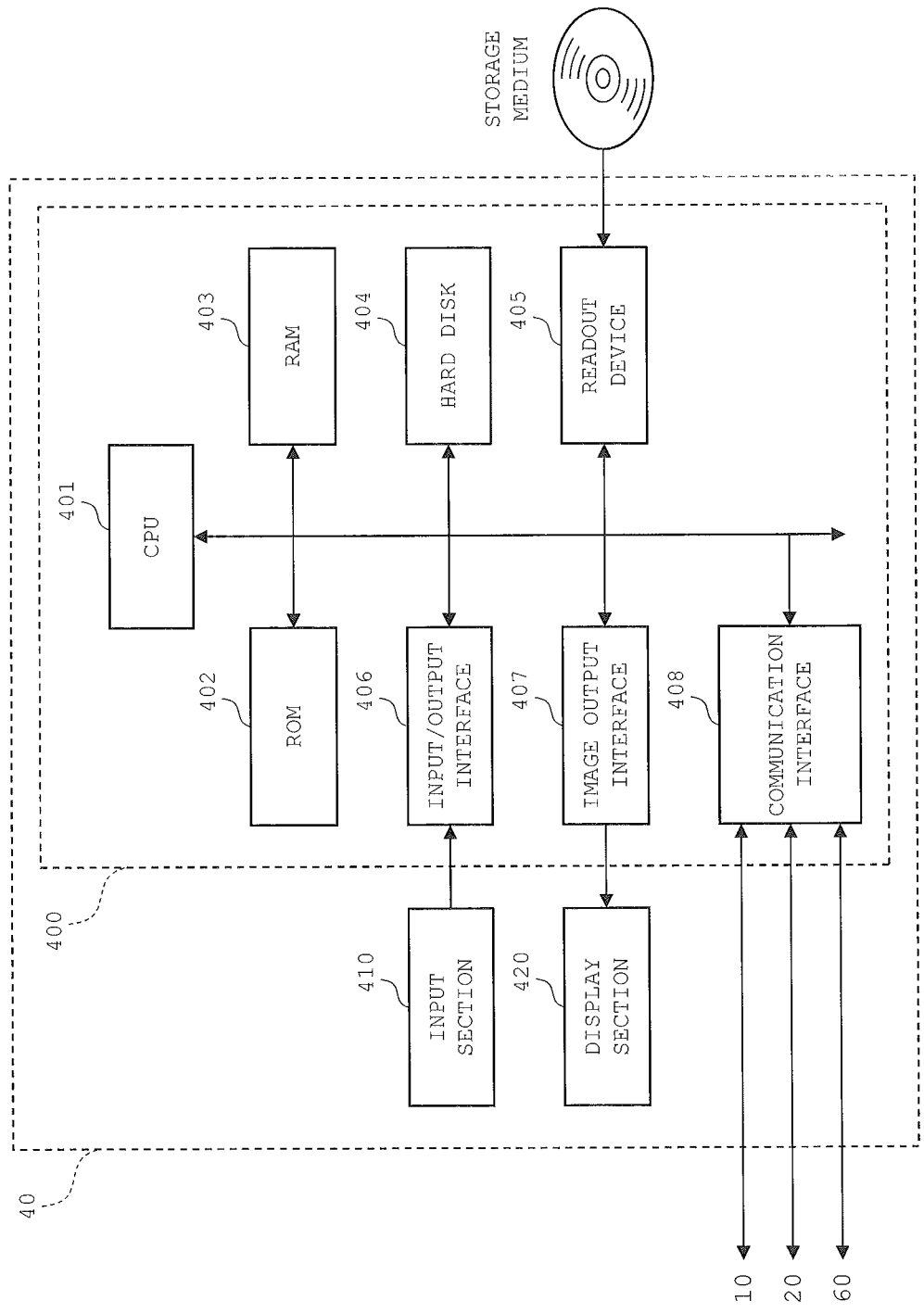
FIG. 5 shows a circuit configuration of an information processing apparatus according to an embodiment.

FIG. 5 shows a circuit configuration of the information processing apparatus 40.

The information processing apparatus 40 is implemented by a personal computer, and includes a body 400, an input section 410, and a display section 420. The body 400 includes a CPU 401, a ROM 402, a RAM 403, a hard disk 404, a readout device 405, an input/output interface 406, an image output interface 407, and a communication interface 408.

The CPU 401 executes computer programs stored in the ROM 402 and computer programs loaded onto the RAM 403. The CPU 401 inquires of the host computer 60 about orders, based on order inquiries received from the first measurement unit 10 and the second measurement unit 20. Further, the CPU 401 transmits the orders received from the host computer 60 to the first measurement unit 10 and the second measurement unit 20.

The RAM 403 is used for reading out computer programs stored in the ROM 402 and the hard disk 404. The RAM 403 is also used as a work area for the CPU 401 when the CPU 401 executes these computer programs.

Various computer programs, such as an operating system and application programs, to be executed by the CPU 401, and data used for execution of such computer programs are installed in the hard disk 404. Moreover, a program for causing the display section 420 to perform display and the like based on an analysis result transmitted from the first measurement unit 10, a program for analyzing a measurement result transmitted from the second measurement unit 20 and for causing the display section 420 to perform display and the like based on the analysis result, and the like are installed in the hard disk 404. Further, a program for displaying a sample insufficiency notification screen 700 (see FIG. 9B), and a program for displaying a process setting screen 800 (see FIG. 12), and the like are installed in the hard disk 404.

The readout device 405 is implemented by a CD drive, a DVD drive, or the like, and can read out computer programs and data stored in a storage medium. The input section 410 implemented by a mouse and a keyboard is connected to the input/output interface 406. By the user using the input section 410, data is inputted to the information processing apparatus 40. The image output interface 407 is connected to the display section 420 implemented by a display and the like, and outputs video signals corresponding to image data to the display section 420. The display section 420 displays an image based on the inputted video signals. Further, the communication interface 408 allows data transmission/reception between the first measurement unit 10, the second measurement unit 20, and the host computer 60.

Figure 6:
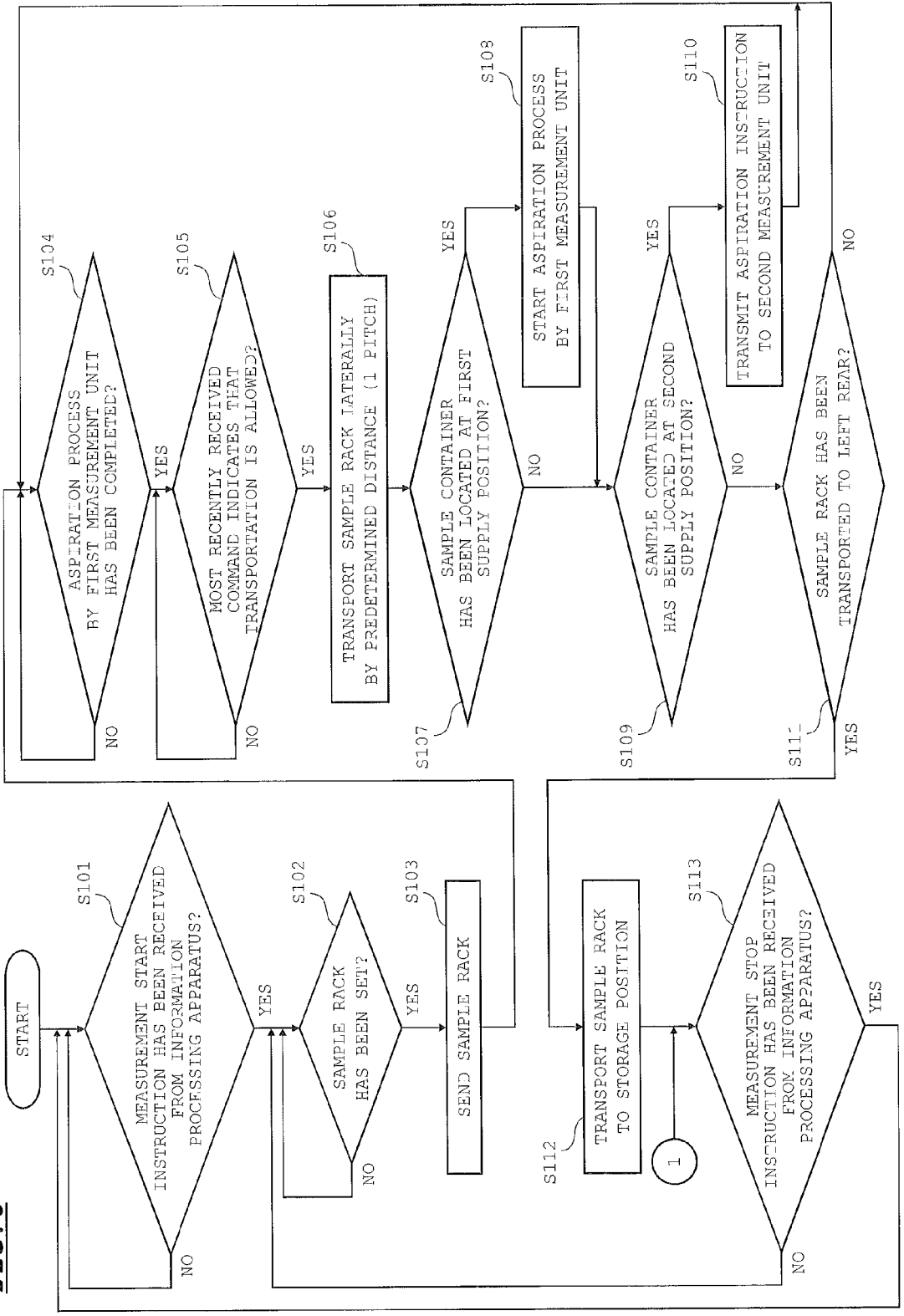
FIG. 6 is a flow chart showing a transport process performed by the first measurement unit according to an embodiment.

FIG. 6 is a flow chart showing a transport process performed by the first measurement unit 10.

The CPU 101a of the first measurement unit 10 causes the process to wait until receiving a measurement start instruction from the information processing apparatus 40 (S101). The measurement start instruction is transmitted from the information processing apparatus 40 to the first measurement unit 10, upon the user inputting an instruction to start measurement via the input section 410 of the information processing apparatus 40.

Subsequently, upon receiving the measurement start instruction (S101: YES), the CPU 101a causes the process to wait until a sample rack 50 is set at the front side of the right vessel region 31a of the transporting apparatus 30. When the sample rack 50 is set at the front side of the right vessel region 31a (S102: YES), the CPU 101a causes the sample rack 50 to be sent to the rear side of the right vessel region 31a (S103).

Subsequently, the CPU 101a causes the process to wait until an aspiration process currently being performed by the first measurement unit 10 is completed (S104). That is, the CPU 101a causes the process to wait until the nozzle 11 is drawn from the corresponding sample container 51 and the sample rack 50 holding the sample container 51 that contains this sample is allowed to move. It should be noted that, after the sample rack 50 was sent to the rear side of the right vessel region 31a in S103 until the aspiration process for the sample container 51 placed at the head (leftmost one) in the sample rack 50 is started, the determination in S104 is kept YES.

Further, the CPU 101a causes the process to wait until a command most recently received from the second measurement unit 20 indicates that transportation is allowed (S105). The command transmitted from the second measurement unit 20 will be described later with reference to FIG. 10. When it has been determined that the command most recently received from the second measurement unit 20 indicates that transportation is allowed (S105: YES), the CPU 101a drives the pushing-out mechanism 34, whereby the sample rack 50 is transported leftward (X-axis positive direction) by a predetermined distance (1 pitch), that is, by the distance corresponding to the interval between holders of the sample rack 50 (S106).

When the sample container 51 is located in front of the bar code reader 109 by being transported in S106, the bar code reader 109 reads the sample number from the bar code label affixed to the sample container 51. Further, based on the driven amount of the pushing-out mechanism 34, the CPU 101a understands which holder of the sample rack 50 is holding the sample container 51 whose sample number was read. Further, based on the read sample number, the CPU 101a inquires of the information processing apparatus 40 about an order for the first measurement unit 10. Then, the CPU 101a receives the order for the first measurement unit 10 from the information processing apparatus 40.

Next, when the sample container 51 is located at the first supply position 36a or the second supply position 36b by being transported in S106, the aspiration process is performed on the sample contained in the sample container 51 located at the corresponding position. It should be noted that when sample containers 51 are concurrently located at the first supply position 36a and the second supply position 36b, the samples contained in the sample containers 51 located at the respective positions can be concurrently aspirated.

That is, the CPU 101a first determines whether the sample container 51 has been located at the first supply position 36a (S107). When the sample container 51 has been located at the first supply position 36a (S107: YES), the CPU 101a causes the first measurement unit 10 to start the aspiration process (S108). On the other hand, when the sample container 51 has not been located at the first supply position 36a (S107: NO), the process is advanced to S109. The aspiration process performed by the first measurement unit 10 will be described later with reference to FIG. 7.

Subsequently, the CPU 101a determines whether the sample container 51 has been located at the second supply position 36b (S109). When the sample container 51 has been located at the second supply position 36b (S109: YES), the CPU 101a transmits an aspiration instruction to the second measurement unit 20 (S110), and the process is returned to S104. On the other hand, when the sample container 51 has not been located at the second supply position 36b (S109: NO), the process is advanced to S111. It should be noted that the aspiration instruction includes the sample number of the sample container 51 located at the second supply position 36b.

When the sample rack 50 has been transported to the left rear (the rear side of the left vessel region 31b) by being transported in S106 (S111: YES), the CPU 101a causes this sample rack 50 to move to a storage position (the front side of the left vessel region 31b) (S112), and the process is advanced to S113. On the other hand, when the sample rack 50 has not been transported to the left rear (S111: NO), the process is returned to S104.

Next, in S113, the CPU 101a determines whether a measurement stop instruction has been received from the information processing apparatus 40. The measurement stop instruction is transmitted from the information processing apparatus 40 to the first measurement unit 10, upon the user inputting an instruction to stop measurement via the input section 410 of the information processing apparatus 40. When the CPU 101a has received the measurement stop instruction (S113: YES), the process is returned to S101. On the other hand, when the CPU 101a has not received the measurement stop instruction (S113: NO), the process is returned to S102. In this manner, the processes S101 to S113 are repeatedly performed.

Figure 7:
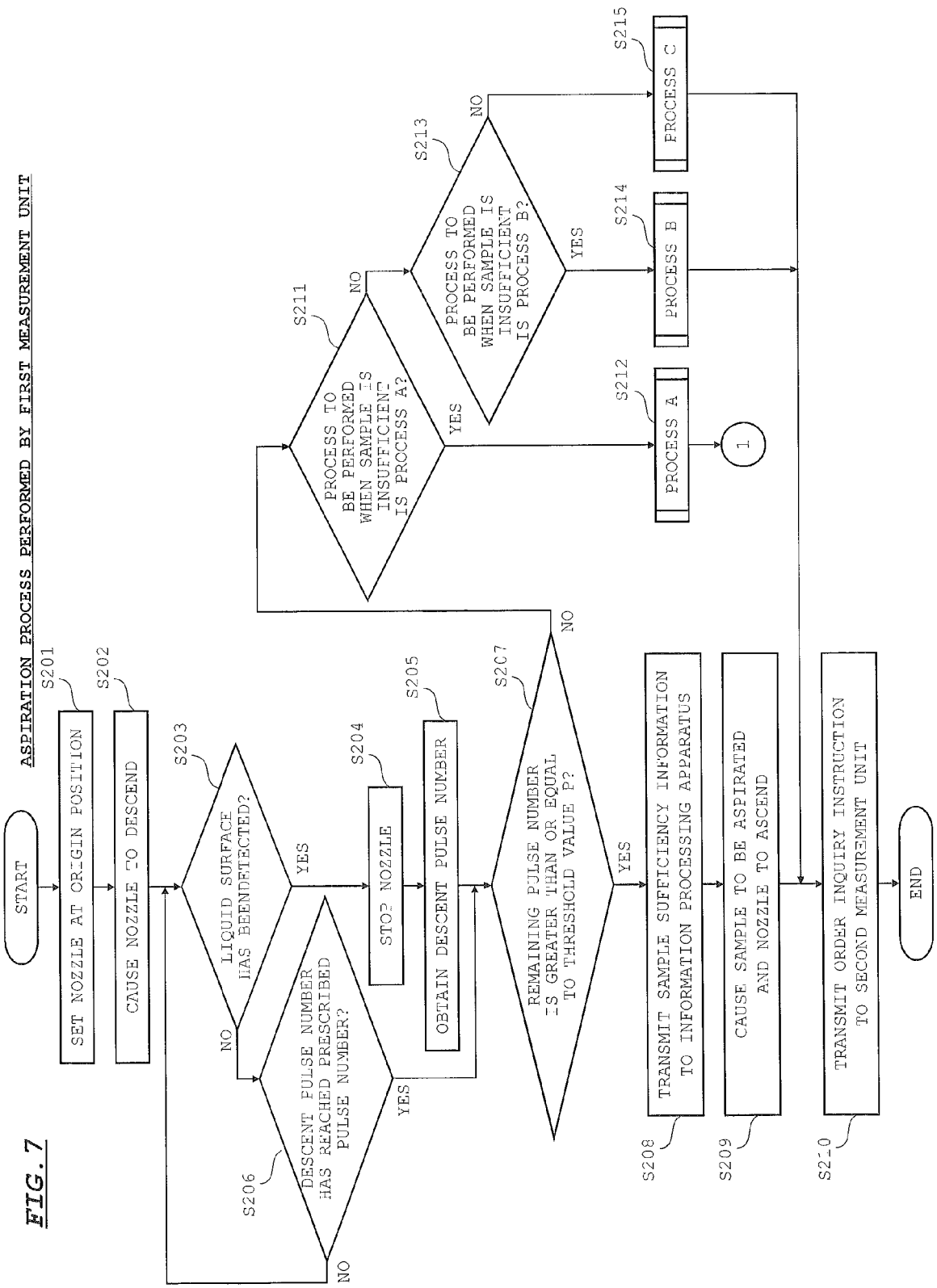
FIG. 7 is a flow chart showing an aspiration process performed by the first measurement unit according to an embodiment.

FIG. 7 is a flow chart showing the aspiration process performed by the first measurement unit 10.

As described with reference to FIGS. 3A and 3B, the CPU 101a of the first measurement unit 10 first causes the nozzle 11 to be set at the origin position (S201). Subsequently, the CPU 101a causes the nozzle 11 to descend (S202). To be specific, the CPU 101a outputs a prescribed pulse number to the controller 107. After resetting the number of pulse signals stored in the memory 107a, the controller 107 continues to output pulse signals to the stepping motor 106 until the number of pulse signals outputted to the stepping motor 106 reaches the prescribed pulse number. Accordingly, the lower end of the nozzle 11 is gradually moved downward from the origin position toward the lower limit position.

Subsequently, the CPU 101a determines whether the liquid surface of the sample has been detected, based on an output signal from the sensor 13 (S203). When the liquid surface has been detected (S203: YES), the CPU 101a causes the controller 107 to stop driving the stepping motor 106, to stop movement of the nozzle 11, even when the descent amount of the nozzle 11 has not reached the amount corresponding to the prescribed pulse number (S204). Further, the CPU 101a obtains a descent pulse number with reference to the memory 107a (S205). On the other hand, when the liquid surface has not been detected (S203: NO), the CPU 101a refers to the memory 107a, and determines, based on information whether pulse signals have been transmitted to the stepping motor 106 by the specified number of pulses, whether the descent pulse number has reached the prescribed pulse number (S206).

When the descent pulse number has not reached the prescribed pulse number (S206: NO), lowering the nozzle 11 is continued and the process is returned to S203. On the other hand, when the descent pulse number has reached the prescribed pulse number (S206: YES), the process is advanced to S207.

Next, in S207, the CPU 101a obtains a remaining pulse number by subtracting the descent pulse number obtained in S205 from the prescribed pulse number, and determines whether the remaining pulse number is greater than or equal to a threshold value P (S207). When it has been determined YES in S206, the remaining pulse number is set to 0, and it is determined NO in S207.

Here, the threshold value P is determined in accordance with a sample amount that will be necessary for performing measurements both in the first measurement unit 10 and the second measurement unit 20. In the present embodiment, the threshold value P is set to a value obtained by adding a predetermined number of pulses P2 to the number of pulses P1 which is necessary to move the nozzle 11 by the height of the liquid surface position that is lowered when aspiration is performed both in the first measurement unit 10 and the second measurement unit 20. The number of pulses P2 is determined in accordance with a dead volume that is necessary to allow aspiration to be performed in the first measurement unit 10 and the second measurement unit 20. It should be noted that the number of pulses P2 may be set to a value obtained by further adding a predetermined value to the value determined in accordance with the dead volume, so as to ensure aspiration to be performed in the first measurement unit 10 and the second measurement unit 20.

When the remaining pulse number is greater than or equal to the threshold value P (S207: YES), the CPU 101a transmits to the information processing apparatus 40 information that a sufficient amount of the sample is contained in the sample container 51 (hereinafter referred to as "sample sufficiency information") (S208). Subsequently, the CPU 101a causes the nozzle 11 to descend below the liquid surface by a distance corresponding to a predetermined number of pulses to aspirate the sample from the sample container 51, and causes the nozzle 11 to ascend after the aspiration is completed (S209). Before causing the sample to be aspirated, the CPU 101a determines whether it is necessary to perform measurement based on the order received from the information processing apparatus 40. Further, after the sample has been aspirated, the CPU 101a causes measurement to be performed based on the order. Further, the CPU 101a analyzes the measurement result, and transmits the analysis result to the information processing apparatus 40.

Subsequently, the CPU 101a transmits an order inquiry instruction to the second measurement unit 20 (S210), and the aspiration process for this sample ends. It should be noted that the order inquiry instruction includes the sample number of the sample container 51 that was subjected to this aspiration process.

On the other hand, when the remaining pulse number is smaller than the threshold value P (S207: NO), the CPU 101a determines which of processes A to C is set as the process to be performed when the sample is insufficient (S211, S213). The process setting when the sample is insufficient is stored in the storage section 101b of the first measurement unit 10 and the hard disk 404 of the information processing apparatus 40.

In the case where the process setting when the sample is insufficient is process A (S211: YES), "process A" is performed (S212). In the case where the process setting when the sample is insufficient is process B (S211: NO, S213: YES), "process B" is performed (S214). In the case where the process setting when the sample is insufficient is process C (S211: NO, S213: NO), "process C" is performed (S215). "Process A", "process B", and "process C" will be described later with reference to FIGS. 8A and 8B.

When "process A" ends, the process is advanced to S112 in FIG. 6. When "process B" or "process C" ends, the CPU 101a transmits an order inquiry instruction to the second measurement unit 20 (S210).

FIG. 8A is a flow chart showing "process A".

The CPU 101a of the first measurement unit 10 transmits to the information processing apparatus 40 information that a sufficient amount of the sample is not contained in the sample container 51 (hereinafter referred to as "sample insufficiency information") (S301). It should be noted that the sample insufficiency information includes the sample number of this sample container 51 and information indicating which holder of the sample rack 50 is holding this sample container 51. Subsequently, the CPU 101a causes the nozzle 11 to ascend without aspirating the sample in the sample container 51 (S302).

Next, the CPU 101a determines whether there is a sample on the sample rack 50 located under the nozzle 11, for which aspiration by the first measurement unit 10 has been completed and aspiration by the second measurement unit 20 has not been completed (S303).

When it has been determined YES in S303, the CPU 101a causes the process to wait until a command most recently received from the second measurement unit 20 indicates that transportation is allowed (S304). When it has been determined that the command most recently received from the second measurement unit 20 indicates that transportation is allowed (S304: YES), the CPU 101a drives the pushing-out mechanism 34, such that, among samples for which aspiration by the first measurement unit 10 has been completed and aspiration by the second measurement unit 20 has not been completed, the sample at the head (leftmost one) is transported to the second supply position 36b (S305). Subsequently, as in S110 in FIG. 6, the CPU 101a transmits an aspiration instruction to the second measurement unit 20 (S306), and the process is returned to S303.

On the other hand, when it has been determined NO in S303, the CPU 101a causes the process to wait until a command most recently received from the second measurement unit 20 indicates that transportation is allowed (S307). When it has been determined that the command most recently received from the second measurement unit 20 indicates that transportation is allowed (S307: YES), the CPU 101a causes the sample rack 50 to be transported to the storage position (the front side of the left vessel region 31b) (S308).

As described above, when "process A" is performed, the aspiration process by the second measurement unit 20 is performed only for samples for which aspiration by the first measurement unit 10 has been completed and aspiration by the second measurement unit 20 has not been completed; and aspirations by the first measurement unit 10 and the second measurement unit 20 are not newly performed for the other samples on the same sample rack 50.

FIG. 8B is a flow chart showing "process B" and "process C".

The CPU 101a of the first measurement unit 10 transmits sample insufficiency information to the information processing apparatus 40 (S311). Subsequently, the CPU 101a causes the nozzle 11 to ascend without aspirating the sample (S312).

As described above, when "process B" or "process C" is performed, aspiration by the first measurement unit 10 is not performed for a sample whose amount is insufficient and which is located at the first supply position 36a. However, in "process B" or "process C", unlike "process A" described above, the aspiration processes by the first measurement unit 10 and the second measurement unit 20 are continued as usual for samples located behind (to the right of) this sample. Further, in "process B" or "process C", the aspiration process by the second measurement unit 20 is performed, as in "process A", also for a sample that is located ahead of (to the left of) this sample and for which aspiration by the first measurement unit 10 has been performed. It should be noted that, in "process B", aspiration by the second measurement unit 20 can be performed for a sample whose amount is insufficient; but in "process C", aspiration by the second measurement unit 20 is not performed for a sample whose amount is insufficient. Whether aspiration is performed in the second measurement unit 20 is determined based on the content of the order generated in FIG. 11.

Figure 9B:
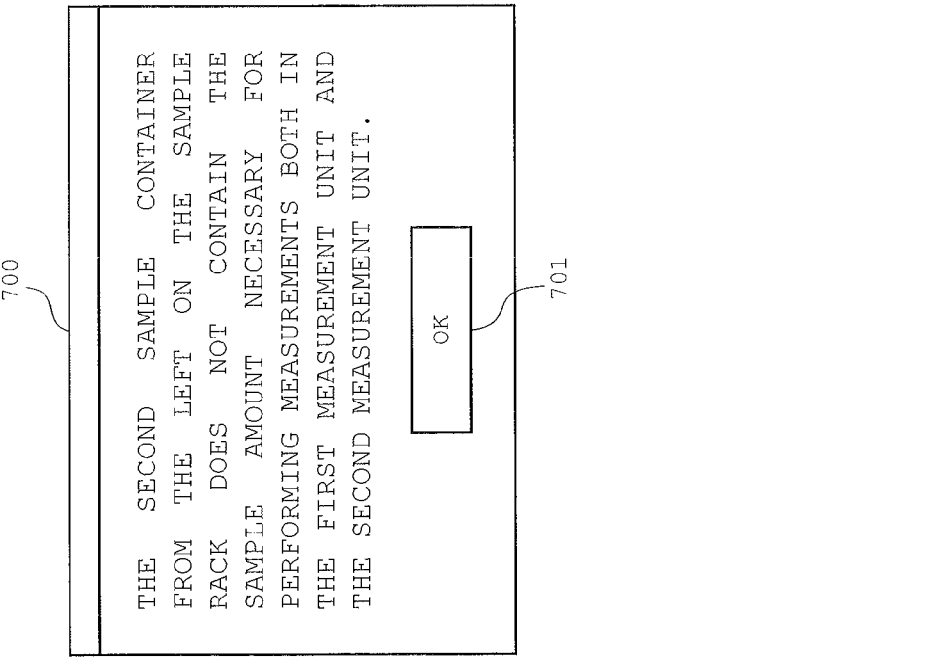
FIG. 9B shows an example of the sample insufficiency notification screen displayed on a display section of the information processing apparatus according to an embodiment.
Figure 9A:
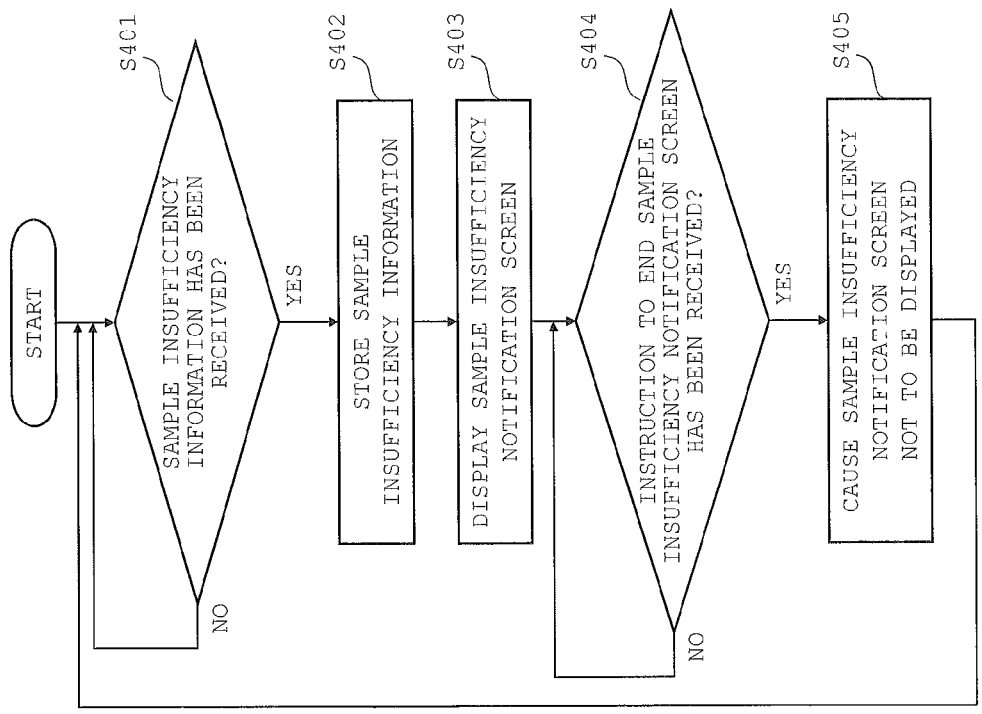
FIG. 9A shows a flow chart showing a process of displaying a sample insufficiency notification screen performed by the information processing apparatus.

FIG. 9A is a flow chart showing a process of displaying a sample insufficiency notification screen performed by the information processing apparatus 40.

When the CPU 401 of the information processing apparatus 40 has received sample insufficiency information transmitted from the first measurement unit 10 in S301 in FIG. 8A and S311 in FIG. 8B (S401: YES), the CPU 401 stores the received sample insufficiency information in the hard disk 404 (S402), and causes the display section 420 to display the sample insufficiency notification screen 700 (S403).

FIG. 9B shows an example of the sample insufficiency notification screen 700 displayed in the display section 420 of the information processing apparatus 40.

As shown in FIG. 9B, a message indicating that there is a sample container 51 that does not contain a sample amount necessary for performing measurements both in the first measurement unit 10 and the second measurement unit 20 is displayed on the sample insufficiency notification screen 700. Further, this message also shows which holder of the sample rack 50 is holding the sample container 51 that does not contain the necessary sample amount. Accordingly, the user can know that a sample container 51 that does not contain the necessary sample amount has been detected, and which holder of the sample rack 50 is holding that sample container 51.

The sample insufficiency notification screen 700 includes an OK button 701. The user can close the sample insufficiency notification screen 700 by pressing the OK button 701.

With reference back to FIG. 9A, when the CPU 401 has received an instruction to end the sample insufficiency notification screen 700 as a result of the user pressing the OK button 701 (S404: YES), the CPU 401 causes the sample insufficiency notification screen 700 not to be displayed (S405). In this manner, the processes S401 to S405 are repeatedly performed.

It should be noted that, also when the CPU 401 has received sample sufficiency information transmitted from the first measurement unit 10 in S208 in FIG. 7, the CPU 401 stores the received sample sufficiency information in the hard disk 404.

FIG. 10 is a flow chart showing the aspiration process performed by the second measurement unit 20.

The CPU 201a of the second measurement unit 20 causes the process to wait until receiving an order inquiry instruction from the first measurement unit 10 (S501). Upon receiving the order inquiry instruction (S501: YES), the CPU 201a inquires, based on the sample number contained in the order inquiry instruction, of the information processing apparatus 40 about an order for the second measurement unit 20 regarding the sample (S502).

Subsequently, the CPU 201a causes the process to wait until receiving the order from the information processing apparatus 40 (S503). Upon receiving the order (S503: YES), the CPU 201a causes the process to wait until receiving an aspiration instruction from the first measurement unit 10 (S504). It should be noted that the order received from the information processing apparatus 40 includes information whether to perform aspiration in the second measurement unit 20.

Upon receiving the aspiration instruction (S504: YES), the CPU 201a writes a command indicating that transportation is not allowed, into a buffer in the storage section 201b of the second measurement unit 20 (S505). It should be noted that either one of a command indicating that transportation is allowed and a command indicating that transportation is not allowed is written in the buffer in the storage section 201b. As an initial value, the command indicating that transportation is allowed is written. The command written in the buffer in the storage section 201b is transmitted to the first measurement unit 10 every predetermined time period.

Next, based on the order received in S503, the CPU 201a determines whether to perform aspiration for the sample located at the second supply position 36b (S506). When it has been determined that aspiration is performed for that sample (S506: YES), the CPU 201a causes the nozzle of the second measurement unit 20 to aspirate the sample from the sample container 51, and causes the nozzle to ascend after the aspiration is completed (S507). After the sample has been aspirated, the CPU 201a causes measurement to be performed based on the order. Further, the CPU 201a transmits the measurement result to the information processing apparatus 40. On the other hand, when it has been determined that aspiration is not performed for that sample (S506: NO), the CPU 201a advances the process to S509.

When the sample has been aspirated and the nozzle has ascended (S507), the CPU 201a causes the process to wait until aspiration by the second measurement unit 20 is completed (S508). That is, the CPU 201a causes the process to wait until the nozzle of the second measurement unit 20 is drawn from the sample container 51 and the sample rack 50 holding the sample container 51 containing this sample is allowed to move. When aspiration by the second measurement unit 20 is completed (S508: YES), the CPU 201a writes the command indicating that transportation is allowed, into the buffer in the storage section 201b of the second measurement unit 20 (S509). In this manner, the processes S501 to S509 are repeatedly performed.

FIG. 11 is a flow chart showing an order process performed by the information processing apparatus 40.

Upon receiving an order inquiry from the second measurement unit 20 (S601: YES), the CPU 401 of the information processing apparatus 40 inquires of the host computer 60 about an order (S602). The CPU 401 causes the process to wait until receiving the order inquired about in S602, from the host computer 60 (S603).

Upon receiving the order from the host computer 60 (S603: YES), the CPU 401 determines whether the amount of the sample contained in the sample container 51 for which this order has been issued is insufficient (S604). The determination is made based on the sample sufficiency information transmitted from the first measurement unit 10 (S208 in FIG. 7) or based on the sample insufficiency information (S301 in FIG. 8A, S311 in FIG. 8B).

When the amount of this sample is not insufficient (S604: NO), the CPU 401 transmits to the second measurement unit 20 an order for this sample including indication to perform aspiration (S605). On the other hand, when the amount of this sample is insufficient (S604: YES), the CPU 401 determines whether the process to be performed when the amount of the sample is insufficient is set to process B (S606). In the case where the process setting when the sample is insufficient is process B (S606: YES), the process is advanced to S605, and an order including indication to perform aspiration is transmitted to the second measurement unit 20. On the other hand, in the case where the process setting when the sample is insufficient is not process B (S606: NO), the CPU 401 transmits indication not to perform aspiration as the order for this sample, to the second measurement unit 20 (S607).

Figure 12:
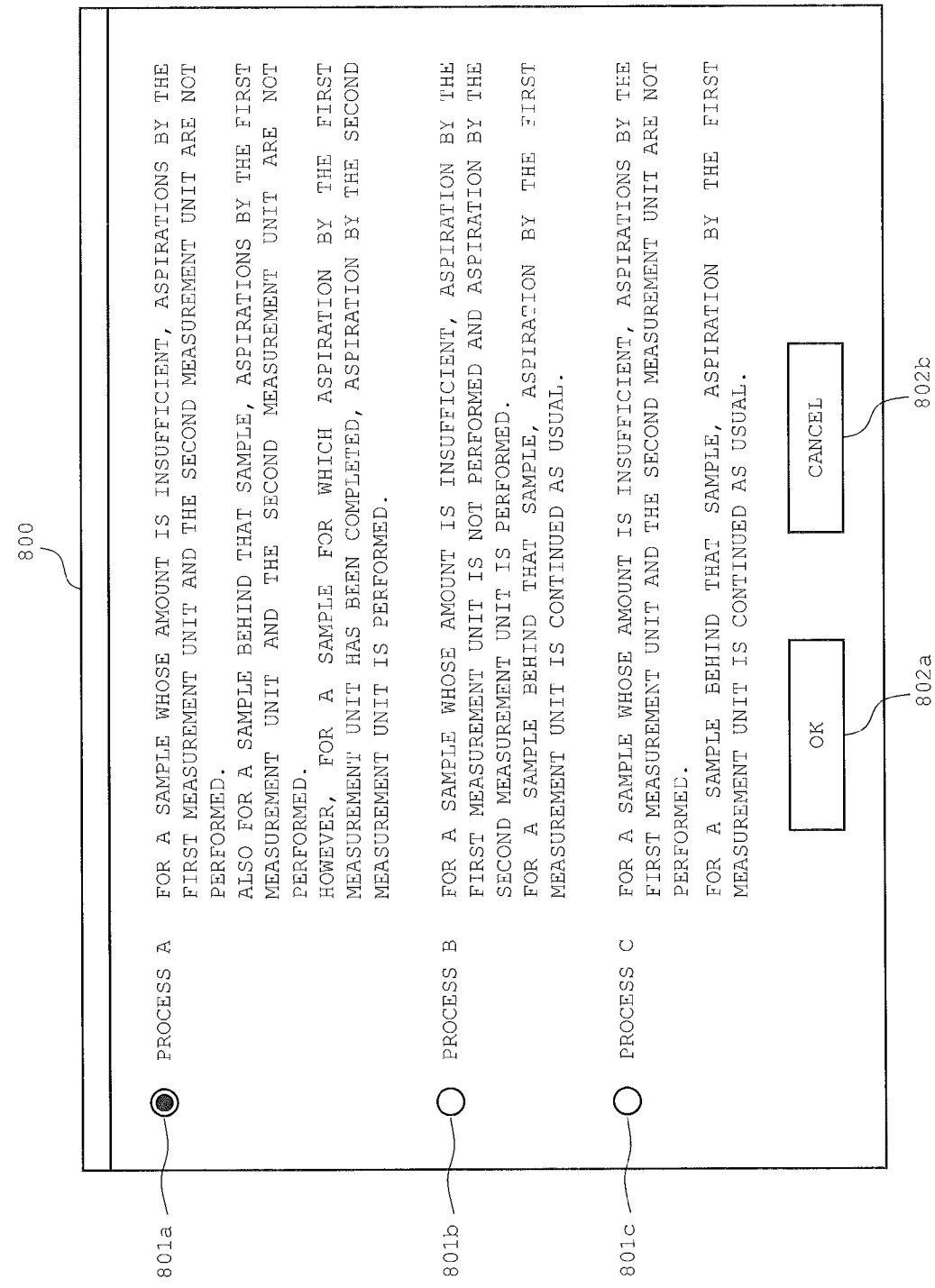
FIG. 12 shows an example of a process setting screen displayed on the display section of the information processing apparatus according to an embodiment.

FIG. 12 shows an example of the process setting screen 800 displayed in the display section 420 of the information processing apparatus 40.

The process setting screen 800 includes radio buttons 801a, 801b, and 801c, an OK button 802a, and a cancel button 802b.

When one of the radio buttons 801a to 801c is pressed by the user, it enters a selected state. The radio buttons 801a to 801c correspond to process A to process C, respectively, and only one of them can be in the selected state. Further, outlines of the contents of process A to process C are shown to the right of the radio buttons 801a to 801c, respectively.

When the OK button 802a is pressed by the user, the process to be performed when the sample is insufficient is changed in accordance with the selected state of the radio button 801a, 801b, or 801c, and the process setting screen 800 is closed. When the cancel button 802b is pressed by the user, the process to be performed when the sample is insufficient is not changed, and the process setting screen 800 is closed.

It should be noted that process A is set by default in the information processing apparatus 40. Therefore, if the user does not change the setting, "process A" is performed, and neither of the first measurement unit 10 nor the second measurement unit 20 aspirates or measures a sample whose amount is insufficient.

FIG. 13A is a flow chart showing a process of displaying the process setting screen 800 performed by the information processing apparatus 40.

The CPU 401 of the information processing apparatus 40 determines whether an instruction to display the process setting screen 800 has been received (S701). The instruction to display the process setting screen 800 is issued by the user via the input section 410 of the information processing apparatus 40. Upon receiving the instruction to display the process setting screen 800 (S701: YES), the CPU 401 inquires of the first measurement unit 10 about the process setting (S702).

Subsequently, the CPU 401 causes the process to wait until receiving the process setting from the first measurement unit 10 (S703). Upon receiving the process setting (S703: YES), the CPU 401 stores the received process setting in the hard disk 404 (S704). Further, the CPU 401 causes the display section 420 to display the process setting screen 800, and sets, based on the received process setting, a corresponding one of the radio buttons 801a to 801c to the selected state (S705).

Next, when the CPU 401 has received an instruction to end the process setting screen 800 as a result of the user pressing the OK button 802a or the cancel button 802b (S706: YES), the CPU 401 determines whether the pressed button is the OK button 802a (S707).

When the OK button 802a has been pressed (S707: YES), the CPU 401 stores the process setting in the hard disk 404 in accordance with the selected state of the radio button 801a, 801b, or 801c (S708). Further, the CPU 401 transmits the process setting stored in the hard disk 404, to the first measurement unit 10 (S709). On the other hand, when the OK button 802a has not been pressed, that is, when the cancel button 802b has been pressed (S707: NO), the process is advanced to S710. In S710, the CPU 401 causes the process setting screen 800 not to be displayed. In this manner, the processes S701 to S710 are repeatedly performed.

FIG. 13B is a flow chart showing a process of transmitting a process setting performed by the first measurement unit 10.

As shown in S702 in FIG. 13A, upon receiving an inquiry about the process setting from the information processing apparatus 40 (S801: YES), the CPU 101a of the first measurement unit 10 transmits the process setting stored in the storage section 101b, to the information processing apparatus 40 (S802).

FIG. 13C is a flow chart showing a process of storing a process setting performed by the first measurement unit 10.

As shown in S709 in FIG. 13A, upon receiving the process setting from the information processing apparatus 40 (S811: YES), the CPU 101a of the first measurement unit 10 stores the received process setting in the storage section 101b (S812).

As described above, according to the present embodiment, with respect to a sample container 51 located at the first supply position 36a, when causing the nozzle 11 to descend, if the remaining pulse number is smaller than the threshold value P (S207 in FIG. 7: NO), that is, if the amount of the sample in the sample container 51 is not sufficient for performing measurements both in the first measurement unit 10 and the second measurement unit 20, the default-set "process A" prevents either of the measurement units from aspirating the sample from the sample container 51. Accordingly, before the sample is aspirated by the first measurement unit 10 and the second measurement unit 20, the user can select an appropriate method. Therefore, it is possible to prevent occurrence of a situation where a sample is obtained from the patient again. An example of the appropriate method includes the following: analysis in one of the first measurement unit 10 and the second measurement unit 20 is performed automatically by using the corresponding measurement unit, and analysis for the other measurement unit is performed manually, instead of automatic analysis. To be specific, when the amount of the sample is not sufficient for performing analysis both in the first measurement unit 10 and the second measurement unit 20, but is sufficient for analysis in one of the measurement units; the user may wish that analysis in the first measurement unit 10, which is for urine qualitative analysis, is performed manually, and analysis in the second measurement unit 20, which is for urinary sediment analysis, is automatically performed by using the second measurement unit 20. In such a case, if urine qualitative analysis is performed manually without causing the first measurement unit 10 to aspirate the sample, and only urinary sediment measurement is separately performed by using the second measurement unit 20 for automatic analysis; it is possible to avoid a situation where a sample is obtained from the patient again in order to perform urinary sediment measurement.

Alternatively, by performing both analyses manually, it is possible to avoid a situation where a sample is obtained from the patient again in order to perform one of the urine qualitative analysis and the urinary sediment analysis.

Further, in the case of "process A", aspirations and measurements by the first measurement unit 10 and the second measurement unit 20 are not performed for samples located behind a sample whose amount has been determined as insufficient. Therefore, it is possible to quickly take out the sample whose amount has been determined as insufficient, and thus, it is possible to quickly take an appropriate measure for that sample.

It should be noted that even in the case where the remaining pulse number is smaller than the threshold value P, when process B has been set by the user, aspiration only by the second measurement unit 20 can be performed. Accordingly, the user can prioritize as appropriate aspiration by the second measurement unit 20 over that by the first measurement unit 10. Further, it is not necessary to set this sample container 51 on the transporting apparatus 30 again in order to perform measurement in the second measurement unit 20. Therefore, it is possible to quickly start processing for a sample whose amount has been determined as insufficient, and to alleviate the burden to the user.

Further, even in the case where the remaining pulse number is smaller than the threshold value P, when process C has been set by the user, aspirations and measurements by the first measurement unit 10 and the second measurement unit 20 can be performed as usual for samples behind a sample whose amount is insufficient. In this case, since it is not necessary to set sample containers 51 located behind the sample whose amount is insufficient, on the transporting apparatus 30 again, it is possible to alleviate the burden to the user.

Further, according to the present embodiment, when a sample is insufficient, the sample insufficiency notification screen 700 shown in FIG. 9B is displayed in the display section 420. Accordingly, the user can easily recognize that there is a sample whose amount is insufficient, and which holder of the sample rack 50 is holding that sample.

Further, according to the present embodiment, the process setting when the sample is insufficient can be changed via the process setting screen 800 shown in FIG. 12. Therefore, the user can cause the sample analyzer 1 to perform a desired process. According to the present embodiment, it is possible to select to set as appropriate the process to be performed when the amount of the sample is insufficient, from "process A", "process B", and "process C". Therefore, it is possible to enhance the convenience for the user.

An embodiment of the present invention has been described. However, the present invention is not limited to the above embodiment.

For example, in the above embodiment, a subject to be measured is exemplified by urine, but a subject to be measured may be blood. That is, the present invention can also be applied to a sample analyzer which tests blood, and further, the present invention can be applied to a clinical sample analyzer which tests other clinical samples.

Further, in the above embodiment, when it has been determined that the amount of the sample is insufficient (S207 in FIG. 7: NO), if process B has been selected as the process setting, aspiration only by the second measurement unit 20 is performed. However, the present invention is not limited thereto. Process D may be provided that allows the first measurement unit 10 to perform aspiration but does not allow the second measurement unit 20 to perform aspiration, and the user may select process D via the process setting screen 800 shown in FIG. 12, as in the case of processes A to C.

Further, in the above embodiment, when it has been determined that the amount of the sample is insufficient, the sample insufficiency notification screen 700 is displayed in the display section 420 of the information processing apparatus 40. However, the present invention is not limited thereto. The color of a portion of the display content in the display section 420 may be changed, or an alarm provided in the sample measurement apparatus 2 may be sounded. When an alarm is provided, the alarm may be sounded only in the case where process A is set as the process setting when the sample is insufficient.

Further, in the above embodiment, the amount of the sample in the sample container 51 is detected by means of the number of pulses supplied by the stepping motor 106. However, the amount of the sample may be detected by another method. For example, the amount of the sample in the sample container 51 can be detected by using the time needed for the nozzle 11 to reach the liquid surface of the sample from the origin position, or the magnitude of the capacitance at the tip of the nozzle 11 when detecting the liquid surface. Alternatively, light or a supersonic wave is used to detect the liquid surface position, or an image of the sample container is taken and the image is analyzed to detect the liquid surface position, whereby the amount of the sample may be detected. Still alternatively, the amount of the sample may be detected by using the weight of the sample and the like.

In addition to the above, various modifications can be made as appropriate without departing from the scope of the technical idea defined by the claims.

What is claimed is:

1. A sample analyzer comprising:
   a first measurement unit configured to perform a first aspiration operation on a sample in a sample container in which the sample in the sample container is aspirated at a first aspiration position for the first measurement unit to perform a first measurement on the aspirated sample;
   a second measurement unit arranged downstream of the first measurement unit along a transport direction and configured to perform a second aspiration operation on the sample in the sample container in which the sample in the sample container is aspirated at a second aspiration position for the second measurement unit to perform a second measurement which is different from the first measurement;
   a transporting apparatus configured to transport a plurality of racks in series in a length direction of the rack along the transport direction from the first measurement unit to the second measurement unit, each rack having a line of holders at a regular pitch for holding a plurality of sample containers including a target sample container, the transporting apparatus being configured to position respective sample containers in each rack at the first and second aspiration positions for the first and second aspiration operations, respectively, by: the first and second measurement units;
   a detection section configured to detect an amount of a sample in each target sample container positioned at the first aspiration position; and
   a control section having a memory that stores a program programming the control section to:
   determine, responsive to a detection result by the detection section whether an amount of a sample left in each target sample container is less than a threshold amount, wherein the threshold amount represents a minimum amount of the sample sufficient for both the first and second measurement units to perform the first and second measurements, respectively, on the sample; and
   upon a respective determination by the control section that a target sample container is a sample-sufficiency container in which the amount of the sample therein is greater than the threshold amount, operate the first and second measurement units and the transporting apparatus to transport the sample-sufficiency container through the first and second measurement units such that the first and second aspiration operations are performed on the sample-sufficiency container, and
   upon a respective determination by the control section that a target sample container is a sample-shortage container in which the amount of the sample therein is less than the threshold amount, implement a selected one of a plurality of different operation settings that represent different policies to be implemented to direct the control section as to how differently to handle sample containers held on racks each holding the sample-shortage container,
   wherein the plurality of different operation settings includes first and second operation settings, the control section further programmed to:
   store the first operation setting in the memory;
   operate the first and second measurement units and the transporting apparatus under the first operation setting to transport a first rack holding a sample-shortage container through the first and second measurement units with neither of the first and second aspiration operations performed on the sample-shortage container held on the first rack;
   replace the first operation setting stored in the memory with the second operation setting; and
   operate the first and second measurement units and the transporting apparatus under the second operation setting to transport a second rack holding a sample-shortage container through the first and second measurement units with only one of the first and second aspiration operations performed on the sample-shortage container held on the second rack.

2. The sample analyzer according to claim 1, further comprising:
   a display; and
   a notification section configured to display a notification of presence of the sample-shortage container on the first rack, wherein the notification identifies the sample-shortage container with an identification of a holder of the first rack holding the sample-shortage container.

3. The sample analyzer according to claim 1, wherein the first measurement unit is a urine qualitative measurement unit, and the second measurement unit is a urinary sediment measurement unit.

4. The sample analyzer according to claim 1, wherein under the first operation setting, the control section is programmed to:
   operate the first and second measurement units against performing the first and second aspiration operations on the sample in the sample-shortage container held on the first rack and on the sample in any subsequent sample container held on the first rack downstream of the sample-shortage container;
   determine whether there is a half-processed sample container held on the first rack upstream of the sample-shortage container, wherein the half-processed container includes a sample that has been aspirated by the first measurement unit but not yet been aspirated by the second measurement unit;
   upon a determination by the control section that there is a half-processed container held on the first rack upstream of the sample-shortage container, operate the transporting apparatus to transfer the first rack in its length direction along the transport direction and position the half-processed sample container on the lack at the second aspiration position; and
   operate the second measurement unit to perform the second aspiration operation on the sample in the half-processed sample container.

5. The sample analyzer according to claim 1, wherein under the second operation setting, the control section is programmed to:
   operate the first measurement unit against performing the first aspiration operation on the sample in the sample-shortage container held on the second rack;
   operate the transporting apparatus to transfer the second rack in its length direction along the transport direction and position the sample-shortage container on the second lack at the second aspiration position; and
   operate the second measurement unit to perform the second aspiration operation on the sample in the sample-shortage container on the second rack;
   determine, responsive to a detection result by the detection section, whether an amount of a sample left in a subsequent sample container held on the second rack downstream of the sample-shortage container is less than the threshold amount; and upon a determination by the control section that the amount of the sample left in the subsequent sample container on the second rack is less than the threshold amount, implement the second operation setting to handle the subsequent sample container on the second rack according to second operation setting.

6. The sample analyzer according to claim 1, wherein the plurality of operation settings includes a third operation setting under which the control section is programmed to:
   replace an operation setting stored in the memory with the third operation setting;
   operate the first and second measurement units against performing the first and second aspiration operations on a sample-shortage container held on a third rack;
   determine, responsive to a detection result by the detection section, whether an amount of a sample left in a subsequent sample container held on the third rack downstream of the sample-shortage container is less than the threshold amount; and
   upon a determination by the control section that the amount of the sample left in the subsequent sample container on the third rack is less than the threshold amount, implement the third operation setting to handle the subsequent sample container on the third rack according to the third operation setting.

7. The sample analyzer according to claim 1 further comprising an information processing apparatus programmed to:
   display the plurality of operation settings on a display for selection by a user;
   receive a selection of an operation setting; and
   send the selection of the operation setting to the control section.

8. A method of analyzing a sample executed by a sample analyzer comprising:
   a first measurement unit configured to perform a first aspiration operation on a sample in a sample container in which the sample in the sample container is aspirated at a first aspiration position for the first measurement unit to perform a first measurement on the aspirated sample;
   a second measurement unit arranged downstream of the first measurement unit along a transport direction and configured to perform a second aspiration operation on the sample in the sample container in which the sample in the sample container is aspirated at a second aspiration position for the second measurement unit to perform a second measurement which is different from the first measurement;
   a transporting apparatus configured to transport a plurality of racks in series in a length direction of the rack along the transport direction from the first measurement unit to the second measurement unit, each rack having a line of holders at a regular pitch for holding a plurality of sample containers including a target sample container, the transporting apparatus being configured to position respective sample containers in each rack at the first and second aspiration positions for the first and second aspiration operations, respectively, by the first and second measurement units; and
   a detection section configured to detect an amount of sample in each target sample container positioned at the first aspiration position,
   the method comprising:
   (a) responsive to a detection result by the detection section, determining whether an amount of a sample left in each target sample container is less than or greater than a threshold amount, wherein the threshold amount represents a minimum amount of the sample sufficient for both the first and second measurement units to perform the first and second measurements, respectively, on the sample;
   (b) upon a respective determination in step (a) that a target sample container is a sample-sufficiency container in which the amount of the sample therein is greater than the threshold amount, operate the first and second measurement units and the transporting apparatus to transport the sample-sufficiency container through the first and second measurement units such that the first and second aspiration operations are performed on the sample-sufficiency container, and
   (c) upon a respective determination in step (a) that a target sample container is a sample-shortage container in which the amount of the sample therein is less than the threshold amount, implementing a selected one of a plurality of different operation settings that represent different policies to be implemented to direct how differently to handle sample containers held on racks each holding the sample-shortage container, wherein the plurality of different operation settings includes first and second operation settings;
   (d) storing the first operation setting in a memory;
   (e) operating the first and second measurement units and the transporting apparatus under the first operation setting to transport a first rack holding a sample-shortage container through the first and second measurement units with neither of the first and second aspiration operations performed on the sample-shortage container held on the first rack;
   (f) replacing the first operation setting stored in the memory with the second operation setting; and
   (g) operating the first and second measurement units and the transporting apparatus under the second operation setting to transport a second rack holding a sample-shortage container through the first and second measurement units with only one of the first and second aspiration operations performed on the sample-shortage container held on the second rack.

9. The method of analyzing a sample according to claim 8, wherein step (e) comprising:
   (e1) operating the first and second measurement units against performing the first and second aspiration operations on the sample in the sample-shortage container held on the first rack and on the sample in any subsequent sample container held on the first rack downstream of the sample-shortage container;
   (e2) determining whether there is a half-processed sample container held on the first rack upstream of the sample-shortage container, wherein the half-processed container includes a sample that has been aspirated by the first measurement unit but not yet been aspirated by the second measurement unit;
   (e3) upon a determination in step (e2) that there is a half-processed container held on the first rack upstream of the sample-shortage container, operating the transporting apparatus to transfer the first rack in its length direction along the transport direction and position the half-processed sample container on the lack at the second aspiration position; and
   operating the second measurement unit to perform the second aspiration operation on the sample in the half-processed sample container.

10. The method of analyzing a sample according to claim 8, wherein step (g) comprising:

(g1) operating the first measurement unit against performing the first aspiration operation on the sample in the sample-shortage container held on the second rack;

(g2) operating the transporting apparatus to transfer the second rack in its length direction along the transport direction and position the sample-shortage container on the second lack at the second aspiration position; and (g3) operating the second measurement unit to perform the second aspiration operation on the sample in the sample-shortage container on the second rack;

(g4) determining, responsive to a detection result by the detection section, whether an amount of a sample left in a subsequent sample container held on the second rack downstream of the sample-storage container is less than the threshold amount; and (g5) upon a determination in step (g4) that the amount of the sample left in the subsequent sample container on the second rack is less than the threshold amount, implementing the second operation setting to handle the subsequent sample container on the second rack according to second operation setting.

11. The method of analyzing a sample according to claim 8, wherein the plurality of operation settings includes a third operation setting under which the method comprises:

(h) replacing an operation setting in the memory with the third operation setting;

(i1) operating the first and second measurement units against performing the first and second aspiration operations on a sample-shortage container held on a third rack;

(i2) responsive to a detection result by the detection section, determining whether an amount of a sample left in a subsequent sample container held on the third rack downstream of the sample-shortage container is less than the threshold amount; and (i3) upon a determination in step (i2) that the amount of the sample left in the subsequent sample container on the third rack is less than the threshold amount, implementing the third operation setting to handle the subsequent sample container on the third rack according to the third operation setting.

* * * * *